United States Patent
Cahoon et al.

(12) 
(10) Patent No.: US 6,545,200 B1
(45) Date of Patent: Apr. 8, 2003

(54) STEROL BIOSYNTHETIC ENZYMES

(75) Inventors: Rebecca E. Cahoon, Wilmington; Omolayo O. Famodu, Newark; Brian McGonigle, Wilmington; J. Antoni Rafalski, Wilmington; Hajime Sakai, Wilmington, all of DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/464,535

(22) Filed: Dec. 15, 1999

Related U.S. Application Data

(60) Provisional application No. 60/112,555, filed on Dec. 16, 1998.

(51) Int. Cl.[7] .......................... A01H 3/00; C07H 21/04; C07K 14/415; C12N 5/14; C12N 9/00
(52) U.S. Cl. ...................... 800/278; 435/69.1; 435/183; 435/410; 435/419; 435/252.3; 435/320.1; 530/350; 530/370; 536/23.6; 536/24.1; 536/24.33; 800/295
(58) Field of Search ................................ 435/69.1, 183, 435/410, 419, 252.3, 320.1; 530/350, 370; 536/23.6, 24.1, 24.33; 800/278, 295

(56) References Cited

PUBLICATIONS

Bork, P. Genome Research, vol. 10, p 398–400, 2000.*
Ashman et al., (1991) Lipids 26:628–632.
Choe T. et al., (1998) Plant Cell 10:231–243.
Labrie et al., (1992) J. Steroid Biochem. Mol. Biol. 41:421–435.
NCBI General Identifier No. 2772934.
Plant Molecular Biology 38(5):807–815 (1998) Grebenok et al.
NCBI General Identifier No. 2935342.
NCBI General Identifier No. 5915851.
Cell 85(2):171–182 (1996) Szekeres et al.
NCBI General Identifier No. 3075392.
Nature 402(6763):761–768 (1999) Lin et al.

* cited by examiner

*Primary Examiner*—Phuong T. Bui

(57) ABSTRACT

This invention relates to an isolated nucleic acid fragment encoding a sterol biosynthetic enzyme. The invention also relates to the construction of a chimeric gene encoding all or a portion of the sterol biosynthetic enzyme, in sense or antisense orientation, wherein expression of the chimeric gene results in production of altered levels of the sterol biosynthetic enzyme in a transformed host cell.

15 Claims, No Drawings

STEROL BIOSYNTHETIC ENZYMES

This application claims priority benefit of U.S. Provisional Application No. 60/112,555 filed Dec. 16, 1998, now pending.

FIELD OF THE INVENTION

This invention is in the field of plant molecular biology. More specifically, this invention pertains to nucleic acid fragments encoding sterol biosynthetic enzymes in plants and seeds.

BACKGROUND OF THE INVENTION

The C-8 sterol isomerase enzyme is involved in plant, animal, and fungal sterol biosynthesis. The product of the ERG2 gene is also called delta 8-delta 7-sterol isomerase, C-8,7 sterol isomerase or D8AE7 isomerase and is non-essential in yeast. This membrane-bound enzyme is required for the isomerization of the delta 8 double bond to the delta 7 position in the distal portion of the ergosterol biosynthesis pathway (Ashman et al. (1991) *Lipids* 26:628–632).

Brassinosteroids are plant enzymes important in growth promotion. Steroid 22-alplha-hydroxylase (DWF4) is a brassinosteroid biosynthetic enzyme, a member of the cytochrome P450 superfamily. The *Arabidopsis thaliana* DWF4 is a cytochrome P450 monooxygenase with significant similarity to the brassinosteroid enzyme CPD. DWF4 contains the four domains characteristic of cytochrome non-A P450 enzymes and is involved in plant sterol biosynthesis functioning as a 22 alpha-hydroxylase in what is probably the rate limiting step in brassinosteroid biosynthesis (Choe t al. (1998) *Plant Cell* 10:231–243).

3-beta hydroxy-delta-5-steroid dehydrogenase (EC 1.1.1.145) is also called progesterone reductase. It is an oxidoreductase which acts on the CH—OH group of donors with NAD+ or NADP+ as acceptors in the C-21 steroid metabolism and the androgen and estrogen metabolisms. The enzyme converts 3 beta hydroxy-5-ene-steroids into 3-keto-4-ene derivatives and interconvers 3 beta-hydroxy and 3-keto-5 alpha-androstane steroids (Labrie et al. (1992) *J. Steroid Biochem. Mol. Biol.* 41:421–435).

SUMMARY OF THE INVENTION

The present invention relates to isolated polynucleotides comprising a nucleotide sequence encoding a polypeptide of at least 40 amino acids that has at least 80% identity based on the Clustal method of alignment when compared to a C-8,7 sterol isomerase polypeptide of SEQ ID NOs:2, 4, 6, 8, 22, 24, 26, and 28. The present invention also relates to an isolated polynucleotide comprising the complement of the nucleotide sequences described above.

The present invention relates to isolated polynucleotides comprising a nucleotide sequence encoding a polypeptide of at least 70 amino acids that has at least 80% identity based on the Clustal method of alignment when compared to a steroid 22-alpha-hydroxylase polypeptide of SEQ ID NOs:10, 12, 14, 30, 32, 34, 36, 38, and 40. The present invention also relates to an isolated polynucleotide comprising the complement of the nucleotide sequences described above.

The present invention relates to isolated polynucleotides comprising a nucleotide sequence encoding a polypeptide of at least 80 amino acids that has at least 80% identity based on the Clustal method of alignment when compared to a 3-beta-hydroxy-delta-5-steroid dehydrogenase polypeptide of SEQ ID NOs:16, 18, 20, 42, and 44. The present invention also relates to an isolated polynucleotide comprising the complement of the nucleotide sequences described above.

It is preferred that the isolated polynucleotides of the claimed invention consist of a nucleic acid sequence selected from the group consisting of SEQ ID NOs:1, 3, 5, 7, 9, 11, 13, 15, 17, 19, 21, 23, 25, 27, 29, 31 33, 35, 37, 39, 41, and 43 that codes for the polypeptide selected from the group consisting of SEQ ID NOs:2, 4, 6, 8, 10, 12, 14, 16, 18, 20, 22, 24, 26, 28, 30, 32, 34, 36, 38, 40, 42, and 44. The present invention also relates to an isolated polynucleotide comprising a nucleotide sequences of at least 60 (preferably at least 40, most preferably at least 30) contiguous nucleotides derived from a nucleotide sequence selected from the group consisting of SEQ ID NOs:1, 3, 5, 7, 9, 11, 13, 15, 17, 19, 21, 23, 25, 27, 29, 31 33, 35, 37, 39, 41, and 43 and the complement of such nucleotide sequences.

The present invention relates to a chimeric gene comprising an isolated polynucleotide of the present invention operably linked to suitable regulatory sequences.

The present invention relates to an isolated host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

The present invention relates to a process for producing an isolated host cell comprising a chimeric gene of the present invention or an isolated polynucleotide of the present invention, the process comprising either transforming or transfecting an isolated compatible host cell with a chimeric gene or isolated polynucleotide of the present invention.

The present invention relates to a C-8,7 sterol isomerase polypeptide of at least 40 amino acids comprising at least 80% homology based on the Clustal method of alignment compared to a polypeptide selected from the group consisting of SEQ ID NOs:2, 4, 6, 8, 22, 24, 26, and 28.

The present invention relates to a Steroid 22-alpha-hydroxylase polypeptide of at least 70 amino acids comprising at least 80% homology based on the Clustal method of alignment compared to a polypeptide selected from the group consisting of SEQ ID NOs:10, 12, 14, 30, 32, 34, 36, 38, and 40.

The present invention relates to a 3-beta-Hydroxy-delta-5-steroid dehydrogenase polypeptide of at least 80 amino acids comprising at least 80% homology based on the Clustal method of alignment compared to a polypeptide selected from the group consisting of SEQ ID NOs:16, 18, 20, 42, and 44.

The present invention relates to a method of selecting an isolated polynucleotide that affects the level of expression of a sterol biosynthetic enzyme polypeptide in a host cell, preferably a plant cell, the method comprising the steps of: (a) constructing an isolated polynucleotide of the present invention or an isolated chimeric gene of the present invention; (b) introducing the isolated polynucleotide or the isolated chimeric gene into a host cell; (c) measuring the level of a C-8,7 sterol isomerase, a steroid 22-alpha-hydroxylase or a 3-beta-hydroxy-delta-5-steroid dehydrogenase polypeptide in the host cell containing the isolated polynucleotide; and (d) comparing the level of a sterol biosynthetic enzyme polypeptide in the host cell containing the isolated polynucleotide with the level of a sterol biosynthetic enzyme polypeptide in the host cell that does not contain the isolated polynucleotide.

The present invention relates to a method of obtaining a nucleic acid fragment encoding a substantial portion of a C-8,7 sterol isomerase, a steroid 22-alpha-hydroxylase or a 3-beta-hydroxy-delta-5-steroid dehydrogenase polypeptide gene, preferably a plant C-8,7 sterol isomerase, steroid 22-alpha-hydroxylase or 3-beta-hydroxy-delta-5-steroid dehydrogenase polypeptide gene, comprising the steps of: synthesizing an oligonucleotide primer comprising a nucleotide sequence of at least 60 (preferably at least 40, most preferably at least 30) contiguous nucleotides derived from a nucleotide sequence selected from the group consisting of SEQ ID NOs:1, 3, 5, 7, 9, 11, 13, 15, 17, 19, 21, 23, 25, 27, 29, 31 33, 35, 37, 39, 41, and 43 and the complement of such nucleotide sequences; and amplifying a nucleic acid fragment (preferably a cDNA inserted in a cloning vector) using the oligonucleotide primer. The amplified nucleic acid fragment preferably will encode a portion of a C-8,7 sterol isomerase, a steroid 22-alpha-hydroxylase or a 3-beta-hydroxy-delta-5-steroid dehydrogenase amino acid sequence.

The present invention also relates to a method of obtaining a nucleic acid fragment encoding all or a substantial portion of the amino acid sequence encoding a C-8,7 sterol isomerase, a steroid 22-alpha-hydroxylase or a 3-beta-hydroxy-delta-5-steroid dehydrogenase polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

A further embodiment of the instant invention is a method for evaluating at least one compound for its ability to inhibit the activity of a C-8,7 sterol isomerase, a steroid 22-alpha-hydroxylase or a 3-beta-hydroxy-delta-5-steroid dehydrogenase, the method comprising the steps of: (a) transforming a host cell with a chimeric gene comprising a nucleic acid fragment encoding a C-8,7 sterol isomerase, a steroid 22-alpha-hydroxylase or a 3-beta-hydroxy-delta-5-steroid dehydrogenase, operably linked to suitable regulatory sequences; (b) growing the transformed host cell under conditions that are suitable for expression of the chimeric gene wherein expression of the chimeric gene results in production of C-8,7 sterol isomerase, steroid 22-alpha-hydroxylase or 3-beta-hydroxy-delta-5-steroid dehydrogenase in the transformed host cell; (c) optionally purifying the C-8,7 sterol isomerase, the steroid 22-alpha-hydroxylase or the 3-beta-hydroxy-delta-5-steroid dehydrogenase expressed by the transformed host cell; (d) treating the C-8,7 sterol isomerase, the steroid 22-alpha-hydroxylase or the 3-beta-hydroxy-delta-5-steroid dehydrogenase with a compound to be tested; and (e) comparing the activity of the C-8,7 sterol isomerase, the steroid 22-alpha-hydroxylase or the 3-beta-hydroxy-delta-5-steroid dehydrogenase that has been treated with a test compound to the activity of an untreated C-8,7 sterol isomerase, steroid 22-alpha-hydroxylase or 3-beta-hydroxy-delta-5-steroid dehydrogenase, thereby selecting compounds with potential for inhibitory activity.

The present invention relates to a composition, such as a hybridization mixture, comprising an isolated polynucleotide of the present invention.

The present invention relates to an isolated polynucleotide of the present invention comprising at least 30 contiguous nucleotides derived from a nucleic acid sequence selected from the group consisting of SEQ ID NOs:1, 3, 5, 7, 9, 11, 13, 15, 17, 19, 21, 23, 25, 27, 29, 31 33, 35, 37, 39, 41, and 43.

The present invention relates to an expression cassette comprising an isolated polynucleotide of the present invention operably linked to a promoter.

The present invention relates to a method for positive selection of a transformed cell comprising: (a) transforming a host cell with the chimeric gene of the present invention or an expression cassette of the present invention; and (b) growing the transformed host cell, preferably plant cell, such as a monocot or a dicot, under conditions which allow expression of the C-8,7 sterol isomerase, the steroid 22-alpha-hydroxylase or the 3-beta-hydroxy-delta-5-steroid dehydrogenase polynucleotide in an amount sufficient to complement a null mutant to provide a positive selection means.

BRIEF DESCRIPTION OF THE SEQUENCE LISTING

The invention can be more fully understood from the following detailed description and the accompanying Sequence Listing which form a part of this application.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

STEROL METABOLISM ENZYMES

| | | SEQ ID NO: | |
| --- | --- | --- | --- |
| Protein | Clone Designation | (Nucleotide) | (Amino Acid) |
| Corn C-8,7 Sterol Isomerase | p0016.ctsco46r | 1 | 2 |
| Rice C-8,7 Sterol Isomerase | rlr24.pk0029.f6 | 3 | 4 |
| Soybean C-8,7 Sterol Isomerase | ses9c.pk001.p11 | 5 | 6 |
| Wheat C-8,7 Sterol Isomerase | Contig of: | 7 | 8 |
| | wre1n.pk0001.e3 | | |
| | wr1.pk0124.f4 | | |
| Corn Steroid 22-Alpha-Hydroxylase | cco1.pk0026.h4 | 9 | 10 |

TABLE 1-continued

STEROL METABOLISM ENZYMES

| Protein | Clone Designation | SEQ ID NO: (Nucleotide) | SEQ ID NO: (Amino Acid) |
|---|---|---|---|
| Rice Steroid 22-Alpha-Hydroxylase | rr1.pk086.j16 | 11 | 12 |
| Wheat Steroid 22-Alpha-Hydroxylase | wdk1c.pk013.e20 | 13 | 14 |
| Corn 3-Beta-Hydroxy-Delta-5-Steroid Dehydrogenase | cen5.pk0025.g9 | 15 | 16 |
| Soybean 3-Beta-Hydroxy-Delta-5-Steroid Dehydrogenase | sgs1c.pk002.113 | 17 | 18 |
| Wheat 3-Beta-Hydroxy-Delta-5-Steroid Dehydrogenase | wlm96.pk028.h21 | 19 | 20 |
| Corn C-8,7 Sterol Isomerase | p0016.ctsco46r:fis | 21 | 22 |
| Rice C-8,7 Sterol Isomerase | rlr24.pk0029.f6:fis | 23 | 24 |
| Soybean C-8,7 Sterol Isomerase | ses9c.pk001.p11:fis | 25 | 26 |
| Wheat C-8,7 Sterol Isomerase | Contig of: wle1.pk0003.e12 wre1n.pk0001.e3:fis | 27 | 28 |
| Corn Steroid 22-Alpha-Hydroxylase | cco1.pk0026.h4:fis | 29 | 30 |
| Corn Steroid 22-Alpha-Hydroxylase | Contig of: cta1.pk0028.d7 p0006.cbysd37r | 31 | 32 |
| Corn Steroid 22-Alpha-Hydroxylase | cta1n.pk0019.e4 | 33 | 34 |
| Rice Steroid 22-Alpha-Hydroxylase | rr1.pk086.j16:fis | 35 | 36 |
| Soybean Steroid 22-Alpha-Hydroxylase | srm.pk0012.a10 | 37 | 38 |
| Wheat Steroid 22-Alpha-Hydroxylase | wdk1c.pk013.e20:fis | 39 | 40 |
| Corn 3-Beta-Hydroxy-Delta-5-Steroid Dehydrogenase | cen5.pk0025.g9:fis | 41 | 42 |
| Soybean 3-Beta-Hydroxy-Delta-5-Steroid Dehydrogenase | sgs1c.pk002.113:fis | 43 | 44 |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "polynucleotide" is a nucleotide sequence such as a nucleic acid fragment. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least 60 contiguous nucleotides, preferably at least 40 contiguous nucleotides, most preferably one of at least 30 contiguous nucleotides derived from SEQ ID NOs:1, 3, 5, 7, 9, 11, 13, 15, 17, 19, 21, 23, 25, 27, 29, 31 33, 35, 37, 39, 41, and 43, or the complement of such sequences.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-a-vis the ability to mediate gene silencing or alteration of the functional properties of the resulting protein molecule. It is therefore understood that the invention encompasses more than the specific exemplary nucleotide or amino acid sequences and includes functional equivalents thereof.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic acid fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least 60 (preferably at least 40, most preferably at least 30) contiguous nucleotides derived from a nucleotide sequence selected from the group consisting of SEQ ID NOs:1, 3, 5, 7, 9, 11, 13, 15, 17, 19, 21, 23, 25, 27, 29, 31 33, 35, 37, 39, 41, and 43 and the complement of such nucleotide sequences may be used in methods of selecting an isolated polynucleotide that affects the expression of a sterol metabolism enzyme polypeptide such as aC-8,7 sterol isomerase, a steroid 22-alpha-hydroxylase or a 3-beta-hydroxy-delta-5-steroid dehydrogenase in a host cell. A method of selecting an isolated polynucleotide that affects the level of expression of a polypeptide in a host cell (eukaryotic, such as plant or yeast, prokaryotic such as bacterial, or viral) may comprise the steps of: constructing an isolated polynucleotide of the present invention or an isolated chimeric gene of the present invention; introducing the isolated polynucleotide or the isolated chimeric gene into a host cell; measuring the level a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6× SSC, 0.5% SDS at room temperature for 15 min, then repeated with 2× SSC, 0.5% SDS at 45° C. for 30 min, and then repeated twice with 0.2× SSC, 0.5% SDS at 50° C. for 30 min. A more preferred set of stringent conditions uses higher temperatures in which the washes are identical to those above except for the temperature of the final two 30 min washes in 0.2× SSC, 0.5% SDS was increased to 60° C. Another preferred set of highly stringent conditions uses two final washes in 0.1× SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least about 50 amino acids, preferably at least about 100 amino acids, more preferably at least about 150 amino acids, still more preferably at least about 200 amino acids, and most preferably at least about 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY.=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post transcriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Over expression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product(s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual;* Cold Spring Harbor Laboratory Press: Cold Spring Harbor, 1989 (hereinafter "Maniatis").

Nucleic acid fragments encoding at least a portion of several sterol biosynthetic enzymes have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other C-8,7 sterol isomerases, steroid 22-alpha-hydroxylases or 3-beta-hydroxy-delta-5-steroid dehydrogenases, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5'

RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least 60 (preferably at least 40, most preferably at least 30) contiguous nucleotides derived from a nucleotide sequence selected from the group consisting of SEQ ID NOs:1, 3, 5, 7, 9, 11, 13, 15, 17, 19, 21, 23, 25, 27, 29, 31 33, 35, 37, 39, 41, and 43 and the complement of such nucleotide sequences may be used in such methods to obtain a nucleic acid fragment encoding a substantial portion of an amino acid sequence of a polypeptide. The present invention relates to a method of obtaining a nucleic acid fragment encoding a substantial portion of a sterol biosynthetic enzyme polypeptide such as a C-8,7 sterol isomerase, a steroid 22-alpha-hydroxylase or a 3-beta-hydroxy-delta-5-steroid dehydrogenase, preferably a substantial portion of a plant polypeptide of a gene, comprising the steps of: synthesizing an oligonucleotide primer comprising a nucleotide sequence of at least 60 (preferably at least 40, most preferably at least 30) contiguous nucleotides derived from a nucleotide sequence selected from the group consisting of SEQ ID NOs:1, 3, 5, 7, 9, 11, 13, 15, 17, 19, 21, 23, 25, 27, 29, 31 33, 35, 37, 39, 41, and 43, and the complement of such nucleotide sequences; and amplifying a nucleic acid fragment (preferably a cDNA inserted in a cloning vector) using the oligonucleotide primer. The amplified nucleic acid fragment preferably will encode a portion of a C-8,7 sterol isomerase, a steroid 22-alpha-hydroxylase or a 3-beta-hydroxy-delta-5-steroid dehydrogenase polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of steroids or brassinosteroids in those cells. Manipulation of the expression of any one of these genes may affect the steroid hormone response enhancing biomass production and grain yield. Changes in the expression patterns of these genes may also result in differences in stress response.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the isolated polynucleotide (or chimeric gene) may be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by directing the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.*100:1627–1632) with or without removing targeting sequences that are already present. While the references cited give examples of each of these, the list is not exhaustive and more targeting signals of use may be discovered in the future.

The instant polypeptides (or portions thereof may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded sterol metabolic enzymes. An example of a vector for high level expression of the instant polypeptides in a bacterial host is provided (Example 8).

Additionally, the instant polypeptides can be used as targets to facilitate design and/or identification of inhibitors of those enzymes that may be useful as herbicides. This is desirable because the polypeptides described herein catalyze various steps in steroid biosynthesis. Accordingly, inhibition of the activity of one or more of the enzymes described herein could lead to inhibition of plant growth. Thus, the instant polypeptides could be appropriate for new herbicide discovery and design.

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide,* Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various African daisy, corn, rice, rubber tree, soybean, and wheat tissues were prepared. The characteristics of the libraries are described below.

TABLE 2 cDNA Libraries from
African Daisy, Corn, Rice, Rubber Tree, Soybean, and Wheat

| Library | Tissue | Clone |
|---|---|---|
| cco1 | Corn Cob of 67 Day Old Plants Grown in Green House | cco1.pk0026.h4 |
| ceb1 | Corn Embryo 10 to 11 Days After Pollination | ceb1.pk0094.e9 |
| cen3n | Corn Endosperm 20 Days After Pollination* | cen3n.pk0178.e9 |
| cen5 | Corn Endosperm 30 Days After Pollination | cen5.pk0025.g9 |
| ces1f | Corn, Stage V19, Immature Ear Shoot | ces1f.pk004.i17 |
| cta1 | Corn Tassel | cta1.pk0028.d7 |

TABLE 2-continued cDNA Libraries from
African Daisy, Corn, Rice, Rubber Tree, Soybean, and Wheat

| Library | Tissue | Clone |
|---|---|---|
| cta1n | Corn Tassel* | cta1n.pk0019.e4 |
| dms1c | African Daisy Developing Seeds | dms1c.pk001.p5 |
| ehb2c | Para rRubber Tree Latex Tapped in Second Day of 2-Day Tapping Cycle | ehb2c.pk013.n19 |
| p0006 | Corn Young Shoot | p0006.cbysd37r |
| p0016 | Corn Tassel Shoots (0.1–1.4 cm), Pooled | p0016.ctsco46r |
| rlr24 | Rice Leaf 15 Days After Germination, 24 Hours After Infection of Strain *Magaporthe grisea* 4360-R-62 (AVR2-YAMO); Resistant | rlr24.pk0029.f6 |
| rr1 | Rice Root of Two Week Old Developing Seedling | rr1.pk086.j16 |
| ses9c | Soybean Embryogenic Suspension | ses9c.pk001.p11 |
| sgs1c | Soybean Seeds 4 Hours After Germination | sgs1c.pk002.l13 |
| sgs2c | Soybean Seeds 14 Hours After Germination | sgs2c.pk003.n17 |
| srm | Soybean Root Meristem | srm.pk0012.a10 |
| wdk1c | Wheat Developing Kernel, 3 Days After Anthesis | wdk1c.pk013.e20 |
| wdk9n | Wheat Kernels 3, 7, 14 and 21 Days After Anthesis | wdk9n.pk001.p2 |
| wle1 | Wheat Leaf From 7 Day Old Etiolated Seedling | wle1.pk0003.e12 |
| wle1n | Wheat Leaf From 7 Day Old Etiolated Seedling* | wle1n.pk0058.f3 |
| wlm96 | Wheat Seedlings 96 Hours After Inoculation With *Erysiphe graminis f.* sp *tritici* | wlm96.pk028.h21 |
| wr1 | Wheat Root From 7 Day Old Seedling | wr1.pk0124.f4 |
| wre1n | Wheat Root From 7 Day Old Etiolated Seedling* | wre1n.pk0001.e3 |

*These libraries were normalized essentially as described in U.S. Pat. No. 5,482,845, incorporated herein by reference.
**Corn developmental stages are explained in the publication "How a corn plant develops" from the Iowa State University Coop. Ext. Service Special Report No. 48 reprinted June 1993.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Example 2

Identification of cDNA Clones cDNA clones encoding sterol biosynthetic enzymes were identified by conducting BLAST (Basic Local Alignment Search Tool; Altschul et al. (1993) *J. Mol. Biol.* 215:403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding C-8,7 Sterol Isomerase

The BLASTX search using the EST sequences from clones listed in Table 3 revealed similarity of the polypeptides encoded by the cDNAs to C-8,7 sterol isomerase from *Arabidopsis thaliana* (NCBI General Identifier No. 2772934). Shown in Table 3 are the BLAST results for individual ESTs ("EST"), or the sequences of contigs assembled from two or more ESTs ("Contig"):

TABLE 3

BLAST Results for Sequences Encoding Polypeptides
Homologous to C-8,7 Sterol Isomerase

| Clone | Status | BLAST pLog Score 2772934 |
|---|---|---|
| p0016.ctsco46r | EST | 39.30 |
| rlr24.pk0029.f6 | EST | 6.00 |
| ses9c.pk001.p11 | EST | 13.70 |
| Contig of:<br>wre1n.pk0001.e3<br>wr1.pk0124.f4 | Contig | 67.70 |

The sequence of the entire cDNA insert in clones p0016.ctsco46r, rlr24.pk0029.f6, ses9c.pk001.p11, and wre1n.pk0001.e3 was determined. Further searching of the DuPont proprietary database allowed the identification of another wheat clone with which to assemble a contig to encode the entire protein. The BLASTP search using sequences from clones listed in Table 4 revealed similarity of the polypeptides encoded by the cDNAs to C-8,7 sterol isomerase from *Arabidopsis thaliana* (NCBI General Identifier No. 2772934). Shown in Table 4 are the BLAST results for the sequences of the entire cDNA inserts comprising the indicated cDNA clones ("FIS") encoding the entire protein, and for a contig assembled from an FIS and one EST encoding the entire protein ("CGS"):

TABLE 4

BLAST Results for Sequences Encoding Polypeptides
Homologous to C-8,7 Sterol Isomerase

| Clone | Status | BLAST pLog Score 2772934 |
|---|---|---|
| p0016.ctsco46r:fis | CGS | 70.15 |
| rlr24.pk0029.f6:fis | CGS | 71.00 |
| ses9c.pk001.p11:fis | CGS | 88.70 |
| Contig of:<br>w1e1.pk0003.e12<br>wre1n.pk0001.e3:fis | CGS* | 71.40 |

The data in Table 5 presents a calculation of the percent identity of the amino acid sequences set forth in SEQ ID NOs:2, 4 6, 8, 22, 24, 26, and 28 and the *Arabidopsis thaliana* sequence (NCBI General Identifier No. 2772934).

TABLE 5

Percent Identity of Amino Acid Sequences Deduced From
the Nucleotide Sequences of cDNA Clones Encoding Polypeptides
Homologous to C-8,7 Sterol Isomerase

| SEQ ID NO. | Percent Identity to 2772934 |
|---|---|
| 2 | 58.3 |
| 4 | 43.2 |
| 6 | 73.5 |
| 8 | 62.0 |
| 22 | 53.4 |
| 24 | 54.8 |
| 26 | 67.1 |
| 28 | 56.5 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and pobabilities indicate that the nucleic acid fragments comprising the instant cDNA clones encode a substantial portion and the entire corn, rice, soybean, and wheat C-8,7 sterol isomerase. These sequences represent the first corn, rice, soybean, and wheat sequences ncoding C-8,7 sterol isomerase.

Example 4

Characterization of cDNA Clones Encoding Steroid 22-Alpha-Hydroxylase

The BLASTX search using the EST sequences from clones listed in Table 6 revealed similarity of the polypeptides encoded by the cDNAs to steroid 22-alpha-hydroxylase from *Arabidopsis thaliana* (NCBI General Identifier No. 2935342). Shown in Table 6 are the BLAST results for individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"):

TABLE 6

BLAST Results for Sequences Encoding Polypeptides
Homologous to Steroid 22-Alpha-Hydroxylase

| Clone | Status | BLAST pLog Score 2935342 |
|---|---|---|
| cco1.pk0026.h4 | EST | 22.52 |
| rr1.pk086.j16 | EST | 44.30 |
| wdk1c.pk013.e20 | EST | 29.30 |

Further sequencing of the above clones and searching of the DuPont proprietary database allowed the identification of other corn steroid 22-alpha-hydroxylases. The BLASTX search using the nucleotide sequences from clones listed in Table 7 revealed similarity of the polypeptides encoded by the cDNAs to steroid 22-alpha-hydroxylase from *Arabidopsis thaliana* (NCBI General Identifier No. 2935342) and to CYP90 from *Arabidopsis thaliana* (NCBI General Identifier No. 5915851). Shown in Table 7 are the BLAST results for individual ESTs ("EST"), the sequences of the entire cDNA inserts comprising the indicated cDNA clones ("FIS"), or the sequences of contigs assembled from two or more ESTs ("Contig"):

TABLE 7

BLAST Results for Sequences Encoding Polypeptides
Homologous to Steroid 22-Alpha-Hydroxylase

| Clone | Status | BLAST pLog Score | |
|---|---|---|---|
| | | 2935342 | 5915851 |
| cco1.pk0026.h4:fis | FIS | 44.52 | 34.00 |
| Contig of:<br>cta1.pk0028.d7<br>p0006.cbysd37r | Contig | 58.15 | 30.00 |
| ctaln.pk0019.e4 | EST | 47.22 | 30.10 |
| rr1.pk086.j16:fis | FIS | 165.00 | 77.52 |

TABLE 7-continued

BLAST Results for Sequences Encoding Polypeptides
Homologous to Steroid 22-Alpha-Hydroxylase

| | | BLAST pLog Score | |
|---|---|---|---|
| Clone | Status | 2935342 | 5915851 |
| srm.pk0012.a10 | EST | 30.70 | 51.00 |
| wdk1c.pk013.e20:fis | FIS | 27.70 | 14.15 |

The data in Table 8 represents a calculation of the percent identity of the amino acid sequences set forth in SEQ ID NOs:10, 12, 14, 30, 32, 34, 36, 38, and 40 and the *Arabidopsis thaliana* sequence (NCBI General Identifier No. 2935342).

TABLE 8

Percent Identity of Amino Acid Sequences Deduced From the Nucleotide Sequences of cDNA Clones Encoding Polypeptides Homologous to Steroid 22-Alpha-Hydroxylase

| SEQ ID NO. | Percent Identity to 2935342 |
|---|---|
| 10 | 56.0 |
| 12 | 78.9 |
| 14 | 70.8 |
| 30 | 51.2 |
| 32 | 63.4 |
| 34 | 59.5 |
| 36 | 72.2 |
| 38 | 46.0 |
| 40 | 60.7 |

Sequence alignments and percent identity calculations were performed using the Megalign program of the LASERGENE bioinformatics computing suite (DNASTAR Inc., Madison, Wis.) Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of corn, rice, soybean, and wheat steroid 22-alpha-hydroxylase. These sequences represent the first corn, rice, soybean, and wheat sequences encoding steroid 22-alpha-hydroxylase.

Example 5

Characterization of cDNA Clones Encoding 3-Beta-Hydroxy-Delta-5-Steroid Dehydrogenase The BLASTX search using the EST sequences from clones listed in Table 9 revealed similarity of the polypeptides encoded by the cDNAs to contig to 3-beta-hydroxy-delta-5-steroid dehydrogenase isolog from *Arabidopsis thaliana* (NCBI General Identifier No. 3075392). Shown in Table 9 are the BLAST results for individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"):

TABLE 9

BLAST Results for Sequences Encoding Polypeptides
Homologous to 3-Beta-Hydroxy-Delta-5-Steroid Dehydrogenase

| Clone | Status | BLAST pLog Score 3075392 |
|---|---|---|
| cen5.pk0025.g9 | EST | 17.40 |
| sgs1c.pk002.113 | EST | 38.52 |
| w1m96.pk028.h21 | EST | 40.10 |

The sequence of the entire cDNA insert in clones cen5.pk0025.g9 and sgs1c.pk002.113 was determined. The BLASTP search using the sequences from clones listed in Table 10 revealed similarity of the polypeptides encoded by the contig to 3-beta-hydroxy-delta-5-steroid dehydrogenase isolog from *Arabidopsis thaliana* (NCBI General Identifier No. 3075392). Shown in Table 10 are the BLAST results for the sequences of the entire cDNA inserts comprising the indicated cDNA clones encoding the entire protein ("CGS"):

TABLE 10

BLAST Results for Sequences Encoding Polypeptides
Homologous to 3-Beta-Hydroxy-Delta-5-Steroid Dehydrogenase

| Clone | Status | BLAST pLog Score 3075392 |
|---|---|---|
| cen5.pk0025.g9:fis | CGS | 101.00 |
| sgs1c.pk002.113:fis | CGS | 162.00 |

The data in Table 11 represents a calculation of the percent identity of the amino acid sequences set forth in SEQ ID NOs:16, 18, 20, 42, and 44 and the *Arabidopsis thaliana* sequence (NCBI General Identifier No. 3075392).

TABLE 11

Percent Identity of Amino Acid Sequences Deduced From the Nucleotide Sequences of cDNA Clones Encoding Polypeptides Homologous to 3-Beta-Hydroxy-Delta-5-Steroid Dehydrogenase

| SEQ ID NO. | Percent Identity to 3075392 |
|---|---|
| 16 | 46.3 |
| 17 | 64.3 |
| 18 | 56.2 |
| 42 | 45.7 |
| 44 | 69.0 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of wheat, and a portion and entire corn and soybean 3-beta-hydroxy-delta-5-steroid dehydrogenase. These sequences represent the first corn, soybean, and wheat sequences encoding 3-beta-hydroxy-delta-5-steroid dehydrogenase.

Example 6

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenasem™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fronun et al. (1990) *Bio/Technology* 25 8:833–839).

Example 7

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli;* Gritz et al.(1 983) Gene 25:179–188) and the 3' region of the nopaline synthase gene from the T-DNA of the Ti plasmid of *Agrobacterium tumefaciens.* The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 8

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Example 9

Evaluating Compounds for their Ability to Inhibit the Activity of Sterol Biosynthetic Enzymes The polypeptides described herein may be produced using any number of methods known to those skilled in the art. Such methods include, but are not limited to, expression in bacteria as described in Example 8, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptides disclosed herein. Assays may be conducted under well known experimental conditions which permit optimal enzymatic activity. For example, assays for C-8,7 sterol isomerase are presented by Ashman et al (1991) *Lipids* 26:628–632. Assays for steroid 22-alpha-hydroxylase are presented by Choe et al. (1998) *Plant Cell* 10:231–243. Assays for 3-beta-hydroxy-delta-5-steroid dehydrogenase are presented by Labrie et al. (1992) *J. Steroid. Biochem. Mol. Biol.* 41:421–435.

Various modifications of the invention in addition to those shown and described herein will be apparent to those skilled in the art from the foregoing description. Such modifications are also intended to fall within the scope of the appended claims.

The disclosure of each reference set forth above is incorporated herein by reference in its entirety.

---

What is claimed is:

1. An isolated polynucleotide comprising:
   (a) a nucleotide sequence encoding a polypeptide having C-8,7 sterol isomerase activity, wherein the amino acid sequence of the polypeptide and the amino acid sequence of SEQ ID NO:22 have at least 80% sequence identity, or
   (b) the complement of the nucleotide sequence, wherein the complement and the nucleotide sequence contain the same number of nucleotides and are 100% complementary.

2. The polynucleotide of claim 1 wherein the sequence identity is at least 85%.

3. The polynucleotide of claim 1 wherein the sequence identity is at least 90%.

4. The polynucleotide of claim 1 wherein the sequence identity is at least 95%.

5. The polynucleotide of claim 1 wherein the polynucleotide encodes the polypeptide of SEQ ID NO:22.

6. The polynucleotide of claim 1 that comprises the nucleotide sequence of SEQ ID NO:21.

7. A recombinant DNA construct comprising the polynucleotide of claim 1 operably linked to at least one regulatory sequence.

8. A cell comprising the polynucleotide of claim 1.

9. The cell of claim 8, wherein the cell is selected from the group consisting of a yeast cell, a bacterial cell and a plant cell.

10. A virus comprising the polynucleotide of claim 1.

11. A transgenic plant comprising the polynucleotide of claim 1.

12. A method for transforming a cell comprising introducing into a cell the polynucleotide of claim 1.

13. A method for producing a transgenic plant comprising (a) transforming a plant cell with the polynucleotide of claim 1 and (b) regenerating a transgenic plant from the transformed plant cell.

14. A vector comprising the polynucleotide of claim 1.

15. A seed comprising the recombinant DNA construct of claim 7.

* * * * *

SEQUENCE LISTING

<160> NUMBER OF SEQ ID NOS: 44

<210> SEQ ID NO 1
<211> LENGTH: 445
<212> TYPE: DNA
<213> ORGANISM: Zea mays

<400> SEQUENCE: 1

```
gccctgttgc ggcgacgact ccgtgactcc tagtccctac ccagatcggc gcccgacgca      60
aggccgagca ggcgatggcc gcagcggcgt caatgggca tccttacgcg ccagccgagc     120
tggaccttcc gggtttcgtg ccgctgaagc tgtcccaggt cgagatcctc gtgtcctacc     180
tcggcgcctc cgtcttcgtt ttcctcgccg tctggctcgt ctccggaaga tgtgtcagat     240
tatccaagac cgaccgtctg ctcatgtgct ggtgggcatt cacagggttg acccacataa     300
tgatcgaggg gccttcgtc ttcactcctg atttcttcaa gaaggagaac cccaatttct     360
ttgatgaagt ttggaaagag tatagtaagg gagactctag gtatgttgct agggacactg     420
caactgttac ggtcgaaggg atcac                                          445
```

<210> SEQ ID NO 2
<211> LENGTH: 115
<212> TYPE: PRT
<213> ORGANISM: Zea mays
<220> FEATURE:
<221> NAME/KEY: UNSURE
<222> LOCATION: (47)..(48)

<400> SEQUENCE: 2

```
Met Gly His Pro Tyr Ala Pro Ala Glu Leu Asp Leu Pro Gly Phe Val
 1               5                  10                  15

Pro Leu Lys Leu Ser Gln Val Glu Ile Leu Val Ser Tyr Leu Gly Ala
            20                  25                  30

Ser Val Phe Val Phe Leu Ala Val Trp Leu Val Ser Gly Arg Xaa Xaa
        35                  40                  45

Ser Lys Thr Asp Arg Leu Leu Met Cys Trp Trp Ala Phe Thr Gly Leu
 50                  55                  60

Thr His Ile Met Ile Glu Gly Pro Phe Val Phe Thr Pro Asp Phe Phe
 65                  70                  75                  80

Lys Lys Glu Asn Pro Asn Phe Phe Asp Glu Val Trp Lys Glu Tyr Ser
                85                  90                  95

Lys Gly Asp Ser Arg Tyr Val Ala Arg Asp Thr Ala Val Thr Val
            100                 105                 110

Glu Gly Ile
        115
```

<210> SEQ ID NO 3
<211> LENGTH: 208
<212> TYPE: DNA
<213> ORGANISM: Oryza sativa
<220> FEATURE:
<221> NAME/KEY: unsure
<222> LOCATION: (123)
<220> FEATURE:
<221> NAME/KEY: unsure
<222> LOCATION: (132)
<220> FEATURE:
<221> NAME/KEY: unsure
<222> LOCATION: (138)
<220> FEATURE:
<221> NAME/KEY: unsure
<222> LOCATION: (160)..(161)
<220> FEATURE:
<221> NAME/KEY: unsure
<222> LOCATION: (164)
<220> FEATURE:
<221> NAME/KEY: unsure
<222> LOCATION: (175)
<220> FEATURE:
<221> NAME/KEY: unsure
<222> LOCATION: (184)..(185)

<400> SEQUENCE: 3

```
ctgctcgatc cgatccaatc cgctcctctc cagtccagat cggaaggaag ccaggaatgg    60
ggcaccccca cccccaccct tacgcgccgg cggagcttca cctcccgggc ttcgtgcctc   120
tcnaactgtc cnaggccnaa atcctcgtgc cctacctcgn nacntccctc ttcancatca   180
tcgnngtggg gctaatctcg ggaaaaat                                      208
```

<210> SEQ ID NO 4
<211> LENGTH: 44
<212> TYPE: PRT
<213> ORGANISM: Oryza sativa
<220> FEATURE:
<221> NAME/KEY: UNSURE

```
<222> LOCATION: (17)
<220> FEATURE:
<221> NAME/KEY: UNSURE
<222> LOCATION: (20)
<220> FEATURE:
<221> NAME/KEY: UNSURE
<222> LOCATION: (22)
<220> FEATURE:
<221> NAME/KEY: UNSURE
<222> LOCATION: (29)
<220> FEATURE:
<221> NAME/KEY: UNSURE
<222> LOCATION: (34)
<220> FEATURE:
<221> NAME/KEY: UNSURE
<222> LOCATION: (37)

<400> SEQUENCE: 4

His Pro Tyr Ala Pro Ala Glu Leu His Leu Pro Gly Phe Val Pro Leu
  1               5                  10                  15

Xaa Leu Ser Xaa Ala Xaa Ile Leu Val Pro Tyr Leu Xaa Thr Ser Leu
             20                  25                  30

Phe Xaa Ile Ile Xaa Val Gly Leu Ile Ser Gly Lys
         35                  40

<210> SEQ ID NO 5
<211> LENGTH: 608
<212> TYPE: DNA
<213> ORGANISM: Glycine max
<220> FEATURE:
<221> NAME/KEY: unsure
<222> LOCATION: (543)
<220> FEATURE:
<221> NAME/KEY: unsure
<222> LOCATION: (552)
<220> FEATURE:
<221> NAME/KEY: unsure
<222> LOCATION: (558)
<220> FEATURE:
<221> NAME/KEY: unsure
<222> LOCATION: (574)..(575)
<220> FEATURE:
<221> NAME/KEY: unsure
<222> LOCATION: (604)
<220> FEATURE:
<221> NAME/KEY: unsure
<222> LOCATION: (606)

<400> SEQUENCE: 5
gtccaactca gtagtcaaca ctaggcactc tctattccca ttcattgcag aagaagatgg      60
aggctcaccc ctacgtccca cgcgatttgc acttacccgg ctacgctccc tgcttccttt     120
ccatgtccaa cattctttcc gtcttcgcct cctcctcatt gctcatcgtc actctcgtct     180
ggatcttctc tggacgcttt aagaaaacca agttgatag agtgctgatg tgctggtggg     240
ccttcacagg tctcacacac attattcttg agggttattt tgttttctct cctgagtttt     300
tcaaggataa aactggcttc tacctggctg aagtttggaa ggaatatagc aaaggggatt     360
caaggtatgc aggaagggat gcaggggtag ttactgttga aggaataaca gcggttttgg     420
agggtccagc tagccttcta gcagtatacg ctatagctac tgggaagtca tatagctaca     480
tacttcagtt tgcatttctt tgggccagct atacggaact gctgtttatt agataacagc     540
aanccttggg anggtganaa ttttccacaa accnngttta caataagcaa actacattgg     600 ggcnantg                                                             608

<210> SEQ ID NO 6
<211> LENGTH: 155
```

<212> TYPE: PRT
<213> ORGANISM: Glycine max

<400> SEQUENCE: 6

```
Ala His Pro Tyr Val Pro Arg Asp Leu His Leu Pro Gly Tyr Ala Pro
  1               5                  10                  15

Cys Phe Leu Ser Met Ser Asn Ile Leu Ser Val Phe Ala Ser Ser Ser
             20                  25                  30

Leu Leu Ile Val Thr Leu Val Trp Ile Phe Ser Gly Arg Lys Lys Thr
         35                  40                  45

Lys Val Asp Arg Val Leu Met Cys Trp Trp Ala Phe Thr Gly Leu Thr
     50                  55                  60

His Ile Ile Leu Glu Gly Tyr Phe Val Phe Ser Pro Glu Phe Lys
 65                  70                  75                  80

Asp Lys Thr Gly Phe Tyr Leu Ala Glu Val Trp Lys Glu Tyr Ser Lys
                 85                  90                  95

Gly Asp Ser Arg Tyr Ala Gly Arg Asp Ala Gly Val Val Thr Val Glu
            100                 105                 110

Gly Ile Thr Ala Val Leu Glu Gly Pro Ala Ser Leu Leu Ala Val Tyr
        115                 120                 125

Ala Ile Ala Thr Gly Lys Ser Tyr Ser Tyr Ile Leu Gln Val Cys Ile
    130                 135                 140

Ser Leu Gly Gln Leu Tyr Gly Thr Ala Val Tyr
145                 150                 155
```

<210> SEQ ID NO 7
<211> LENGTH: 711
<212> TYPE: DNA
<213> ORGANISM: Triticum aestivum
<220> FEATURE:
<221> NAME/KEY: unsure
<222> LOCATION: (476)
<220> FEATURE:
<221> NAME/KEY: unsure
<222> LOCATION: (551)
<220> FEATURE:
<221> NAME/KEY: unsure
<222> LOCATION: (584)
<220> FEATURE:
<221> NAME/KEY: unsure
<222> LOCATION: (620)
<220> FEATURE:
<221> NAME/KEY: unsure
<222> LOCATION: (643)
<220> FEATURE:
<221> NAME/KEY: unsure
<222> LOCATION: (659)
<220> FEATURE:
<221> NAME/KEY: unsure
<222> LOCATION: (681)
<220> FEATURE:
<221> NAME/KEY: unsure
<222> LOCATION: (690)
<220> FEATURE:
<221> NAME/KEY: unsure
<222> LOCATION: (694)
<220> FEATURE:
<221> NAME/KEY: unsure
<222> LOCATION: (699)

<400> SEQUENCE: 7

```
gccgtctggc tcctctccgg gagatgccgc aggttgtccg ggaccgaccg cctgctcatg      60
tgctggtggg cgttcaccgg cctcacccac atactcatcg aggggccctt cgtctttacc     120
cccgatttct tcaccaagac caaccccaac ttcttcgacg aagtctggaa ggagtacagc     180
```

```
aagggtgact ccaggtacgt cgccagggac accgccaccg tcaccgtcga gggaatcacg    240
gccgtgctga aaggccctgc ctcgctgctc gcagtctatg ctatcgcatc gcgcaagtcc    300
tacagccaca tcctccagtt cgccgtatgc ctcggtcagc tctacggatg catcgtctac    360
ttcaccaccg cctacttgga cggcttcaac ttctgggcca gtccgttcta cttctgggca    420
tatttcatcg gcgcaaacag ttcgtggatt gtgataccgt tgctgattgc acgnangagc    480
tggaagaaga tatgtgcggc cgttcatcaa agcgagaagg tcaagacaaa taattctgca    540
acagcatata nggttggtgc aacaagcacac actgaacttc ttgnttatca cagaaattgc    600
tccctgtatt gtacccttan aacacattgt cgaacaagta tcngtacaat aacattgtnc    660
cctctgccta aatgtagaca ntttgcacan acgnggatnt taccacttga g            711
```

<210> SEQ ID NO 8
<211> LENGTH: 158
<212> TYPE: PRT
<213> ORGANISM: Triticum aestivum
<220> FEATURE:
<221> NAME/KEY: UNSURE
<222> LOCATION: (150)

<400> SEQUENCE: 8

```
Arg Arg Leu Ser Gly Thr Asp Arg Leu Leu Met Cys Trp Trp Ala Phe
  1               5                  10                  15

Thr Gly Leu Thr His Ile Leu Ile Glu Gly Pro Phe Val Phe Thr Pro
             20                  25                  30

Asp Phe Phe Thr Lys Thr Asn Pro Asn Phe Phe Asp Glu Val Trp Lys
         35                  40                  45

Glu Tyr Ser Lys Gly Asp Ser Arg Tyr Val Ala Arg Asp Thr Ala Thr
     50                  55                  60

Val Thr Val Glu Gly Ile Thr Ala Val Leu Lys Gly Pro Ala Ser Leu
 65                  70                  75                  80

Leu Ala Val Tyr Ala Ile Ala Ser Arg Lys Ser Tyr Ser His Ile Leu
                 85                  90                  95

Gln Phe Ala Val Cys Leu Gly Gln Leu Tyr Gly Cys Ile Val Tyr Phe
            100                 105                 110

Thr Thr Ala Tyr Leu Asp Gly Phe Asn Phe Trp Ala Ser Pro Phe Tyr
        115                 120                 125

Phe Trp Ala Tyr Phe Ile Gly Ala Asn Ser Ser Trp Ile Val Ile Pro
    130                 135                 140

Leu Leu Ile Ala Thr Xaa Ser Trp Lys Lys Ile Cys Ala Ala
145                 150                 155
```

<210> SEQ ID NO 9
<211> LENGTH: 394
<212> TYPE: DNA
<213> ORGANISM: Zea mays
<220> FEATURE:
<221> NAME/KEY: unsure
<222> LOCATION: (154)
<220> FEATURE:
<221> NAME/KEY: unsure
<222> LOCATION: (160)
<220> FEATURE:
<221> NAME/KEY: unsure
<222> LOCATION: (180)
<220> FEATURE:
<221> NAME/KEY: unsure
<222> LOCATION: (191)
<220> FEATURE:
<221> NAME/KEY: unsure
<222> LOCATION: (202)

```
<220> FEATURE:
<221> NAME/KEY: unsure
<222> LOCATION: (246)
<220> FEATURE:
<221> NAME/KEY: unsure
<222> LOCATION: (282)
<220> FEATURE:
<221> NAME/KEY: unsure
<222> LOCATION: (291)
<220> FEATURE:
<221> NAME/KEY: unsure
<222> LOCATION: (293)..(294)
<220> FEATURE:
<221> NAME/KEY: unsure
<222> LOCATION: (316)
<220> FEATURE:
<221> NAME/KEY: unsure
<222> LOCATION: (323)
<220> FEATURE:
<221> NAME/KEY: unsure
<222> LOCATION: (333)
<220> FEATURE:
<221> NAME/KEY: unsure
<222> LOCATION: (345)..(346)
<220> FEATURE:
<221> NAME/KEY: unsure
<222> LOCATION: (360)
<220> FEATURE:
<221> NAME/KEY: unsure
<222> LOCATION: (366)..(367)
<220> FEATURE:
<221> NAME/KEY: unsure
<222> LOCATION: (373)
<220> FEATURE:
<221> NAME/KEY: unsure
<222> LOCATION: (383)
<220> FEATURE:
<221> NAME/KEY: unsure
<222> LOCATION: (385)

<400> SEQUENCE: 9
gagcacgaca gcataagatc caacaaaggc aaggaggagt gcttgacttc agaagactac      60
aagaagatgg aatataccca acaagtcatc aacgaggcgc tgagatgcgg caacatcgtc     120
aagttcgtcc accggaaggc gctgaaagac gtcnaatacn aagagtatct gattccatcn     180
ggctggaagg ncctaccggt cntcactgcc gttcatctga acccctcact tcatggagac     240
gcgcanagtt tcagccctgt aggtgggagg gcacaagcca anggacaagc nanngttta     300 caccccttggt ggtggnccccg ggntgcccag gtnagagtcc taaanngggc tgcttttttcn     360 ccatannttg ccncattata gtngngagtg tggg                                 394

<210> SEQ ID NO 10
<211> LENGTH: 84
<212> TYPE: PRT
<213> ORGANISM: Zea mays
<220> FEATURE:
<221> NAME/KEY: UNSURE
<222> LOCATION: (41)
<220> FEATURE:
<221> NAME/KEY: UNSURE
<222> LOCATION: (43)
<220> FEATURE:
<221> NAME/KEY: UNSURE
<222> LOCATION: (53)
<220> FEATURE:
<221> NAME/KEY: UNSURE
<222> LOCATION: (57)
<220> FEATURE:
<221> NAME/KEY: UNSURE
<222> LOCATION: (71)
<220> FEATURE:
<221> NAME/KEY: UNSURE
<222> LOCATION: (83)
```

<400> SEQUENCE: 10

| Glu | Glu | Cys | Leu | Thr | Ser | Glu | Asp | Tyr | Lys | Lys | Met | Glu | Tyr | Thr | Gln |
|---|---|---|---|---|---|---|---|---|---|---|---|---|---|---|---|
| 1 | | | | 5 | | | | | 10 | | | | | 15 | |

| Gln | Val | Ile | Asn | Glu | Ala | Leu | Arg | Cys | Gly | Asn | Ile | Val | Lys | Phe | Val |
|---|---|---|---|---|---|---|---|---|---|---|---|---|---|---|---|
| | | | 20 | | | | | 25 | | | | | 30 | | |

| His | Arg | Lys | Ala | Leu | Lys | Asp | Val | Xaa | Tyr | Xaa | Glu | Tyr | Leu | Ile | Pro |
|---|---|---|---|---|---|---|---|---|---|---|---|---|---|---|---|
| | | 35 | | | | | 40 | | | | | 45 | | | |

| Ser | Gly | Trp | Lys | Xaa | Leu | Pro | Val | Xaa | Thr | Ala | Val | His | Leu | Asn | Pro |
|---|---|---|---|---|---|---|---|---|---|---|---|---|---|---|---|
| | 50 | | | | | 55 | | | | | 60 | | | | |

| Ser | Leu | His | Gly | Asp | Ala | Xaa | Ser | Phe | Ser | Pro | Val | Gly | Gly | Arg | Ala |
|---|---|---|---|---|---|---|---|---|---|---|---|---|---|---|---|
| 65 | | | | | 70 | | | | | 75 | | | | | 80 |

| Gln | Ala | Xaa | Gly |
|---|---|---|---|

<210> SEQ ID NO 11
<211> LENGTH: 453
<212> TYPE: DNA
<213> ORGANISM: Oryza sativa
<220> FEATURE:
<221> NAME/KEY: unsure
<222> LOCATION: (203)
<220> FEATURE:
<221> NAME/KEY: unsure
<222> LOCATION: (307)
<220> FEATURE:
<221> NAME/KEY: unsure
<222> LOCATION: (339)
<220> FEATURE:
<221> NAME/KEY: unsure
<222> LOCATION: (366)
<220> FEATURE:
<221> NAME/KEY: unsure
<222> LOCATION: (390)
<220> FEATURE:
<221> NAME/KEY: unsure
<222> LOCATION: (399)
<220> FEATURE:
<221> NAME/KEY: unsure
<222> LOCATION: (416)
<220> FEATURE:
<221> NAME/KEY: unsure
<222> LOCATION: (429)
<220> FEATURE:
<221> NAME/KEY: unsure
<222> LOCATION: (433)
<220> FEATURE:
<221> NAME/KEY: unsure
<222> LOCATION: (441)
<220> FEATURE:
<221> NAME/KEY: unsure
<222> LOCATION: (443)
<220> FEATURE:
<221> NAME/KEY: unsure
<222> LOCATION: (449)

<400> SEQUENCE: 11

| gcagaacgag gggaggctgt tcgagtgcag ctacccgcgc agcatcggcg gcatcctggg | 60 |
|---|---|
| caagtggtcc atgctggtcc tcgtcgggga cccgcaccgc gagatgcgcg ccatctccct | 120 |
| caacttcctc tcctccgtcc gcctccgcgc cgtcctcctc cccgaggtcg agcgccacac | 180 |
| cctcctcgtc ctccgcgcct ggnccccttc ctccaccttc tccgctcaag caccaagcca | 240 |
| agaagttcac gttcaacctg atggcgaaga acataatgag catggacccg ggggagggag | 300 |
| aaacggngcg gctgcggcgg ggagtacatc accttcatna aggggtggt ctccgcgccg | 360 |
| ctcaanctgg ccgggacgcc ctactggaan ggtctcaant ccgtgctggc aattcncggg | 420 |
| ggtaataana ggnaaattgg nangaagcng gtt | 453 |

<210> SEQ ID NO 12
<211> LENGTH: 76
<212> TYPE: PRT
<213> ORGANISM: Oryza sativa
<220> FEATURE:
<221> NAME/KEY: UNSURE
<222> LOCATION: (68)

<400> SEQUENCE: 12

Gln Asn Glu Gly Arg Leu Phe Glu Cys Ser Tyr Pro Arg Ser Ile Gly
1               5                   10                  15

Gly Ile Leu Gly Lys Trp Ser Met Leu Val Leu Val Gly Asp Pro His
            20                  25                  30

Arg Glu Met Arg Ala Ile Ser Leu Asn Phe Leu Ser Ser Val Arg Leu
        35                  40                  45

Arg Ala Val Leu Leu Pro Glu Val Glu Arg His Thr Leu Leu Val Leu
    50                  55                  60

Arg Ala Trp Xaa Pro Ser Ser Thr Phe Ser Ala Gln
65                  70                  75

<210> SEQ ID NO 13
<211> LENGTH: 436
<212> TYPE: DNA
<213> ORGANISM: Triticum aestivum

<400> SEQUENCE: 13
cttcaaccct tggagatgga agggcaacgc atccggcgtg gcgcagaaca gcaacttcat      60
gccctacggc ggcggcacca ggctctgcgc cgggtcggag ctcgccaagc tcgagatggc     120
catcttcctg caccacctgg tgctcaactt ccggtgggag ctcgccgagc cggaccaggc     180
gttcgtctac ccgttcgtcg acttccccaa gggcctgccc atcagggtcc ataggattgc     240
acaggaggaa gaaggagaag agtaaagcgt tttgaccgtg gacatatatg atcggtgctt     300
cagtctagcg tctaggggag aagtatacag aggaaatgta cacatgtccg tccttgtttt     360
cttttccttt ggggtttgtg ttatgtagat gggataaaca aagatgctaa gggtattacc     420
ataaagaaga aatgtt                                                     436

<210> SEQ ID NO 14
<211> LENGTH: 72
<212> TYPE: PRT
<213> ORGANISM: Triticum aestivum

<400> SEQUENCE: 14

Gly Asn Ala Ser Gly Val Ala Gln Asn Ser Asn Phe Met Pro Tyr Gly
1               5                   10                  15

Gly Gly Thr Arg Leu Cys Ala Gly Ser Glu Leu Ala Lys Leu Glu Met
            20                  25                  30

Ala Ile Phe Leu His His Leu Val Leu Asn Phe Arg Trp Glu Leu Ala
        35                  40                  45

Glu Pro Asp Gln Ala Phe Val Tyr Pro Phe Val Asp Phe Pro Lys Gly
    50                  55                  60

Leu Pro Ile Arg Val His Arg Ile
65                  70

<210> SEQ ID NO 15
<211> LENGTH: 390
<212> TYPE: DNA
<213> ORGANISM: Zea mays

-continued

```
<220> FEATURE:
<221> NAME/KEY: unsure
<222> LOCATION: (324)
<220> FEATURE:
<221> NAME/KEY: unsure
<222> LOCATION: (367)

<400> SEQUENCE: 15
caaagatctg aataataatg ggttcgctcc gtgatggcaa gaccaacagc agcagtggcc      60
ggcggtggtg cgcggtgacc ggcggccggg gcttcatggc gaggcacctg gtggccgcgc    120
tgctgcgctc cggcgagtgg cttgtgcggg tcaccgacct cgccccggat gtcgtgctcg    180
gcctcggcga caccgaggac gtcctcgatg acgccctccg tgatggccgc gccgtctatg    240
cctcagcgga tgtctgcaac ctagaccagc ttattcaact tttgaagggg ttgaggttgt    300
tttcacacag ctgctcggat caancaagaa cgaccagcaa cttcactata aggtaacgtt    360 gagggnaaa gacgtggtta tcgtcatatt                                     390

<210> SEQ ID NO 16
<211> LENGTH: 82
<212> TYPE: PRT
<213> ORGANISM: Zea mays

<400> SEQUENCE: 16
```

Arg Trp Cys Ala Val Thr Gly Gly Arg Gly Phe Met Ala Arg His Leu
 1               5                  10                  15

Val Ala Ala Leu Leu Arg Ser Gly Glu Trp Leu Val Arg Val Thr Asp
             20                  25                  30

Leu Ala Pro Asp Val Val Leu Gly Leu Gly Asp Thr Glu Asp Val Leu
         35                  40                  45

Asp Asp Ala Leu Arg Asp Gly Arg Ala Val Tyr Ala Ser Ala Asp Val
     50                  55                  60

Cys Asn Leu Asp Gln Leu Ile Gln Leu Leu Lys Gly Leu Arg Leu Phe
 65                  70                  75                  80

Ser His

```
<210> SEQ ID NO 17
<211> LENGTH: 537
<212> TYPE: DNA
<213> ORGANISM: Glycine max
<220> FEATURE:
<221> NAME/KEY: unsure
<222> LOCATION: (33)
<220> FEATURE:
<221> NAME/KEY: unsure
<222> LOCATION: (72)
<220> FEATURE:
<221> NAME/KEY: unsure
<222> LOCATION: (148)
<220> FEATURE:
<221> NAME/KEY: unsure
<222> LOCATION: (162)
<220> FEATURE:
<221> NAME/KEY: unsure
<222> LOCATION: (345)
<220> FEATURE:
<221> NAME/KEY: unsure
<222> LOCATION: (400)
<220> FEATURE:
<221> NAME/KEY: unsure
<222> LOCATION: (414)
<220> FEATURE:
<221> NAME/KEY: unsure
<222> LOCATION: (417)
<220> FEATURE:
<221> NAME/KEY: unsure
```

```
<222> LOCATION: (470)
<220> FEATURE:
<221> NAME/KEY: unsure
<222> LOCATION: (489)
<220> FEATURE:
<221> NAME/KEY: unsure
<222> LOCATION: (500)
<220> FEATURE:
<221> NAME/KEY: unsure
<222> LOCATION: (502)
<220> FEATURE:
<221> NAME/KEY: unsure
<222> LOCATION: (505)
<220> FEATURE:
<221> NAME/KEY: unsure
<222> LOCATION: (518)

<400> SEQUENCE: 17
gttggaatga ggtgagcgtt gtgtttgagt tancttgact atggaagcaa aagataagtg      60
gtgcgtggtg ancggaggtc gcggcttcgc tgctcggcat ttggtggaaa tgctaattcg     120
tcacaaggag tactgcgttc gcatcgcnga tttggaagtc ancattgttc tcgagcccgc     180
cgagcagtta ggccttctcg ccaggccct gcactctggc cgagcccaat atgtctccct      240
cgatcttcgc aacaaggccc aagttctaaa agcgttggag ggagttgagg tggtgttcca    300
catggtctgc tccaaactct tccattaaca agctaccagc ttcancattc cgtcaatgtg    360
caagggacta ataatgtcat cgatgcttgc gtggagctgn cacgtgaagc gtcncgntta    420
cactaagctc tctcgtttac aacaagctct cccaacgtct tcctccgacn atggttcaag    480
ggaattcana atgggaaacn anaanaatgc cttatgcnca ttcgcctaaa tgatcaa      537

<210> SEQ ID NO 18
<211> LENGTH: 84
<212> TYPE: PRT
<213> ORGANISM: Glycine max
<220> FEATURE:
<221> NAME/KEY: UNSURE
<222> LOCATION: (7)
<220> FEATURE:
<221> NAME/KEY: UNSURE
<222> LOCATION: (37)

<400> SEQUENCE: 18

Asp Lys Trp Cys Val Val Xaa Gly Gly Arg Gly Phe Ala Ala Arg His
  1               5                  10                  15

Leu Val Glu Met Leu Ile Arg His Lys Glu Tyr Cys Val Arg Ile Ala
                 20                  25                  30

Asp Leu Glu Val Xaa Ile Val Leu Glu Pro Ala Glu Gln Leu Gly Leu
             35                  40                  45

Leu Gly Gln Ala Leu His Ser Gly Arg Ala Gln Tyr Val Ser Leu Asp
     50                  55                  60

Leu Arg Asn Lys Ala Gln Val Leu Lys Ala Leu Glu Gly Val Glu Val
 65                  70                  75                  80

Val Phe His Met

<210> SEQ ID NO 19
<211> LENGTH: 525
<212> TYPE: DNA
<213> ORGANISM: Triticum aestivum
<220> FEATURE:
<221> NAME/KEY: unsure
<222> LOCATION: (466)
<220> FEATURE:
<221> NAME/KEY: unsure
<222> LOCATION: (485)
```

<220> FEATURE:
<221> NAME/KEY: unsure
<222> LOCATION: (501)

<400> SEQUENCE: 19

```
ctggtgccga attcggcacg aggccgcgcc gcctacttct ctgtcgacgt ctgcgaatta      60
gcccagctta caaaagcttt ggaaggggta gatactgttt tccacactgc tgcggcggat     120
cataccaaca acaacttcca acttcattac aaggttaatg tcgagggtac aaggaatgtc     180
atcgaggctt gtaacacatg caaggttaaa acactctatt atactagttc cagtggagtt     240
gtattcgatg gagttcatgg cctctttggc gtagacgaat ctacaccgta tccagataag     300
tttcccgacg catacacaga gacaaaggca agaagcagaa aagatggtga taaagtccaa     360
cggaagaaat gagcttctca cttgctgtat acgtcctggc agcatttttg ggtcctggag     420
acacgatagt gccaattttg tgatcttatg gaggaatgat gatcantgtt ggtgatggca     480
agaantgtga tgattttgta natgttgaag aatgtaccca aggtc                     525
```

<210> SEQ ID NO 20
<211> LENGTH: 130
<212> TYPE: PRT
<213> ORGANISM: Triticum aestivum

<400> SEQUENCE: 20

```
Gly Arg Ala Ala Tyr Phe Ser Val Asp Val Cys Glu Leu Ala Gln Leu
  1               5                  10                  15

Thr Lys Ala Leu Glu Gly Val Asp Thr Val Phe His Thr Ala Ala Ala
             20                  25                  30

Asp His Thr Asn Asn Asn Phe Gln Leu His Tyr Lys Val Asn Val Glu
         35                  40                  45

Gly Thr Arg Asn Val Ile Glu Ala Cys Asn Thr Cys Lys Val Lys Thr
     50                  55                  60

Leu Ile Tyr Thr Ser Ser Ser Gly Val Val Phe Asp Gly Val His Gly
 65                  70                  75                  80

Leu Phe Gly Val Asp Glu Ser Thr Pro Tyr Pro Asp Lys Phe Pro Asp
                 85                  90                  95

Ala Tyr Thr Glu Thr Arg Gln Glu Ala Glu Lys Met Val Ile Lys Ser
            100                 105                 110

Asn Gly Arg Asn Glu Leu Leu Thr Cys Cys Ile Arg Pro Gly Ser Ile
        115                 120                 125

Phe Gly
    130
```

<210> SEQ ID NO 21
<211> LENGTH: 895
<212> TYPE: DNA
<213> ORGANISM: Zea mays

<400> SEQUENCE: 21

```
ccacgcgtcc gccctgttgc ggcgacgact ccgtgactcc tagtccctac ccagatcggc      60
gcccgacgca aggccgagca ggcgatggcc gcagcggcgt caatgggcca tccttacgcg     120
ccagccgagc tggaccttcc gggtttcgtg ccgctgaagc tgtcccaggt cgagatcctc     180
gtgtcctacc tcggcgcctc cgtcttcgtt ttcctcgccg tctggctcgt ctccggaaga     240
tgtgtcagat tatccaagac cgaccgtctg ctcatgtgct ggtgggcatt cacagggttg     300
acccacataa tgatcgaggg gcccttcgtc ttcactcctg atttcttcaa gaaggagaac     360
```

```
cccaatttct tgatgaagt ttggaaagag tatagtaagg gagactctag gtatgttgct      420
agggacactg caactgttac ggtcgaaggg atcaccgctg tattggaagg ccctgcatca      480
ctacttgctg tctacgctat tgcatccagg aagtccttca gccacattct ccagttcgcc      540
gtctgtctgg gccagctcta cggatgcctg gtttacttca tcaccgcgta cttggacagc      600
ttcaacttct gggtcggccc gttctacttc tgggcgtatt tcattggcgc aaacagcttc      660
tggatctgga taccgatgct catcgccata aggtcctgga agaaaacttg cgccgcgttt      720
caagctgaga aggtgaagaa gaccaaataa aagctgtctt tagctaccgt tttattggag      780
accgtcattt tgatggctta aattcttgtg ttggttggta ctggaaactg catgatgtac      840
tctttgctca aacaaatgaa gaccggttta caaattcaaa aaaaaaaaaa aaaag          895
```

<210> SEQ ID NO 22
<211> LENGTH: 221
<212> TYPE: PRT
<213> ORGANISM: Zea mays

<400> SEQUENCE: 22

```
Met Ala Ala Ala Ser Met Gly His Pro Tyr Ala Pro Ala Glu Leu
 1               5                  10                  15

Asp Leu Pro Gly Phe Val Pro Lys Leu Ser Gln Val Glu Ile Leu
            20                  25                  30

Val Ser Tyr Leu Gly Ala Ser Val Phe Val Phe Leu Ala Val Trp Leu
        35                  40                  45

Val Ser Gly Arg Cys Val Arg Leu Ser Lys Thr Asp Arg Leu Leu Met
    50                  55                  60

Cys Trp Trp Ala Phe Thr Gly Leu Thr His Ile Met Ile Glu Gly Pro
65                  70                  75                  80

Phe Val Phe Thr Pro Asp Phe Lys Lys Glu Asn Pro Asn Phe Phe
                85                  90                  95

Asp Glu Val Trp Lys Glu Tyr Ser Lys Gly Asp Ser Arg Tyr Val Ala
            100                 105                 110

Arg Asp Thr Ala Thr Val Thr Val Glu Gly Ile Thr Ala Val Leu Glu
        115                 120                 125

Gly Pro Ala Ser Leu Leu Ala Val Tyr Ala Ile Ala Ser Arg Lys Ser
    130                 135                 140

Phe Ser His Ile Leu Gln Phe Ala Val Cys Leu Gly Gln Leu Tyr Gly
145                 150                 155                 160

Cys Leu Val Tyr Phe Ile Thr Ala Tyr Leu Asp Ser Phe Asn Phe Trp
                165                 170                 175

Val Gly Pro Phe Tyr Phe Trp Ala Tyr Phe Ile Gly Ala Asn Ser Phe
            180                 185                 190

Trp Ile Trp Ile Pro Met Leu Ile Ala Ile Arg Ser Trp Lys Lys Thr
        195                 200                 205

Cys Ala Ala Phe Gln Ala Glu Lys Val Lys Lys Thr Lys
    210                 215                 220
```

<210> SEQ ID NO 23
<211> LENGTH: 1039
<212> TYPE: DNA
<213> ORGANISM: Oryza sativa

<400> SEQUENCE: 23

```
ctgctcgatc cgatccaatc cgctcctctc cagtccagat cggaaggaag ccaggaatgg      60
ggcaccccca cccccaccct tacgcgccgg cggagcttca cctcccgggc ttcgtgcctc     120
```

```
tccaactgtc ccaggcccaa atcctcgtgc cctacctcgc cacctccctc ttcctcctcc    180
tcgccgtctg gctcatctcc gggagatgca gtcgtaggct ttccgacacc gaccgctggc    240
tcatgtgctg gtgggccttc accggcctca cccacattat catcgaggga acctttgtct    300
ttgctcctaa tttcttctcc aaccaaaacc cttcttactt cgatgaagtt tggaaagagt    360
acagcaaagg tgactccaga tatgtcgcca gagaccctgc tactgttaca gttgaaggaa    420
ttacagctgt cttggaaggc cctgcttcac tccttgctgt ctatgccatc gcatcgggca    480
agtcctacag ccatatcctc cagttcactg tctgtcttgg tcagctctat ggatgcctgg    540
tgtactttat tacagcctac ttggatggct tcaacttctg gactagcccg ttctacttct    600
gggcttattt cattggtgca aacagctcgt gggttgttat accaactatg atcgccataa    660
ggagctggaa gaagatttgt gcagcatttc aaggtgaaaa ggtgaagact aaataggcaa    720
aggtgcacc ttagtcacag tttggttgga aattaataga catttgtgct atgaacaaca    780
tcattgttcc tgcaattgaa acccttgtgt tactgaaaaa ttgcattgta cccttggagg    840
gaacatcagt gttaattgga tgtgacttta tgcagctatt atgtattgct gcaaagaaa    900
ttgggttttg tttatcctct atcattcaag ctcgctcttc tttacccttg aagaaataaa    960
agggcaggga gttgccattt tgaaaaaaaa aaaaaaaaaa aaaaaaaaaa aaaaaaaaaa   1020
aaaaaaaaaa aaaaaaaaa                                                1039

<210> SEQ ID NO 24
<211> LENGTH: 219
<212> TYPE: PRT
<213> ORGANISM: Oryza sativa

<400> SEQUENCE: 24

Met Gly His Pro His Pro His Pro Tyr Ala Pro Ala Glu Leu His Leu
 1               5                  10                  15

Pro Gly Phe Val Pro Leu Gln Leu Ser Gln Ala Gln Ile Leu Val Pro
                20                  25                  30

Tyr Leu Ala Thr Ser Leu Phe Leu Leu Leu Ala Val Trp Leu Ile Ser
            35                  40                  45

Gly Arg Cys Ser Arg Arg Leu Ser Asp Thr Asp Arg Trp Leu Met Cys
        50                  55                  60

Trp Trp Ala Phe Thr Gly Leu Thr His Ile Ile Ile Glu Gly Thr Phe
 65                  70                  75                  80

Val Phe Ala Pro Asn Phe Phe Ser Asn Gln Asn Pro Ser Tyr Phe Asp
                85                  90                  95

Glu Val Trp Lys Glu Tyr Ser Lys Gly Asp Ser Arg Tyr Val Ala Arg
                100                 105                 110

Asp Pro Ala Thr Val Thr Val Glu Gly Ile Thr Ala Val Leu Glu Gly
            115                 120                 125

Pro Ala Ser Leu Leu Ala Val Tyr Ala Ile Ala Ser Gly Lys Ser Tyr
        130                 135                 140

Ser His Ile Leu Gln Phe Thr Val Cys Leu Gly Gln Leu Tyr Gly Cys
145                 150                 155                 160

Leu Val Tyr Phe Ile Thr Ala Tyr Leu Asp Gly Phe Asn Phe Trp Thr
                165                 170                 175

Ser Pro Phe Tyr Phe Trp Ala Tyr Phe Ile Gly Ala Asn Ser Ser Trp
            180                 185                 190

Val Val Ile Pro Thr Met Ile Ala Ile Arg Ser Trp Lys Lys Ile Cys
        195                 200                 205
```

```
Ala Ala Phe Gln Gly Glu Lys Val Lys Thr Lys
    210                 215
```

<210> SEQ ID NO 25
<211> LENGTH: 993
<212> TYPE: DNA
<213> ORGANISM: Glycine max

<400> SEQUENCE: 25

```
gcacgaggtc caactcagta gtcaacacta ggcactctct attcccattc attgcagaag     60
aagatggagg ctcacccta cgtcccacgc gatttgcact acccggcta cgctccctgc     120
ttcctttcca tgtccaacat tctttccgtc ttcgcctcct cctcattgct catcgtcact    180
ctcgtctgga tcttctctgg acgctttaag aaaaccaaag ttgatagagt gctgatgtgc    240
tggtgggcct tcacaggtct cacacacatt attcttgagg gttatttgt tttctctcct    300
gagttttca aggataaaac tggcttctac ctggctgaag tttggaagga atatagcaaa    360
ggggattcaa ggtatgcagg aagggatgca ggggtagtta ctgttgaagg aataacagcg    420
gttttggagg gtccagctag ccttctagca gtatacgcta tagctactgg gaagtcatat    480
agctacatac ttcagtttgc catttctttg ggccagctat acggaactgc tgtttattat    540
ataacagcaa tcttggaagg tgataatttt tctacaaact cgttttacta ttatgcatac    600
tacattggag caaatgcctc ctggattgta atacccttga tcattgccat ccgctgctgg    660
aggaagatct gtgcagcatt tcgagttcaa ggtggccaga caaaaaagcc taaagttcgt    720
tgaaggaaac attttcaggt tattggtctt agagatcctg agctaataat gatgttttgg    780
ggtagttgag ataggagaga ttgttgtaag aattgtgaca ttgattctct taaactgcat    840
atctcaggga gaaaaaaaa atcccagtgt catttgagaa ggtgatgttt taattttaa     900
gttttgaata agtattttcc tatcattgat ttgaaattga atattgaatg ttagctggca    960
gatgctagaa tataaaaaaa aaaaaaaaa aaa                                   993
```

<210> SEQ ID NO 26
<211> LENGTH: 219
<212> TYPE: PRT
<213> ORGANISM: Glycine max

<400> SEQUENCE: 26

```
Met Glu Ala His Pro Tyr Val Pro Arg Asp Leu His Leu Pro Gly Tyr
  1               5                  10                  15

Ala Pro Cys Phe Leu Ser Met Ser Asn Ile Leu Ser Val Phe Ala Ser
             20                  25                  30

Ser Ser Leu Leu Ile Val Thr Leu Val Trp Ile Phe Ser Gly Arg Phe
         35                  40                  45

Lys Lys Thr Lys Val Asp Arg Val Leu Met Cys Trp Trp Ala Phe Thr
     50                  55                  60

Gly Leu Thr His Ile Ile Leu Glu Gly Tyr Phe Val Phe Ser Pro Glu
 65                  70                  75                  80

Phe Phe Lys Asp Lys Thr Gly Phe Tyr Leu Ala Glu Val Trp Lys Glu
                 85                  90                  95

Tyr Ser Lys Gly Asp Ser Arg Tyr Ala Gly Arg Asp Ala Gly Val Val
            100                 105                 110

Thr Val Glu Gly Ile Thr Ala Val Leu Glu Gly Pro Ala Ser Leu Leu
        115                 120                 125

Ala Val Tyr Ala Ile Ala Thr Gly Lys Ser Tyr Ser Tyr Ile Leu Gln
```

```
                    130                 135                 140
Phe Ala Ile Ser Leu Gly Gln Leu Tyr Gly Thr Ala Val Tyr Tyr Ile
145                 150                 155                 160

Thr Ala Ile Leu Glu Gly Asp Asn Phe Ser Thr Asn Ser Phe Tyr Tyr
                165                 170                 175

Tyr Ala Tyr Tyr Ile Gly Ala Asn Ala Ser Trp Ile Val Ile Pro Leu
            180                 185                 190

Ile Ile Ala Ile Arg Cys Trp Arg Lys Ile Cys Ala Ala Phe Arg Val
        195                 200                 205

Gln Gly Gly Gln Thr Lys Lys Pro Lys Val Arg
    210                 215
```

<210> SEQ ID NO 27
<211> LENGTH: 889
<212> TYPE: DNA
<213> ORGANISM: Triticum aestivum

<400> SEQUENCE: 27

```
gttgactagc gctgatttgc tccctctcca gctccggctc ccagatcgag acggcggcgg     60
cggcggcgat gggcgcccac ccttacgtgc cggcgagcct ggacctcccg ggctacgtgc    120
cgctgcgcct cacccagctc gagatcctcg ggcctacctc cggcacctcc ctcttcgtcc    180
tcgtcgccgt ctggctcctc tccgggagat gccgcaggtt gtccgggacc gaccgcctgc    240
tcatgtgctg gtgggcgttc accggcctca cccacatact catcgagggg cccttcgtct    300
ttaccccga tttcttcacc aagaccaacc ccaacttctt cgacgaagtc tggaaggagt    360
acagcaaggg tgactccagg tacgtcgcca gggacaccgc caccgtcacc gtcgagggaa    420
tcacggccgt gctgaaaggc cctgcctcgc tgctcgcagt ctatgctatc gcatcgcgca    480
agtcctacag ccacatcctc cagttcgccg tatgcctcgg tcagctctac ggatgcatcg    540
tctacttcac caccgcctac ttggacggct tcaacttctg ggccagtccg ttctacttct    600
gggcatattt catcggcgca aacagttcgt ggattgtgat accgttgctg atcgccacga    660
ggagctggaa gaagatatgt gcggccgttc atcaaagcga gaaggtcaag accaaataat    720
tcctgcaaca ggcatatagg gtttggctgc aaccaagaca cactgaactt cttgttttat    780
caccagaaat ttgcttcctt gtattgtacc ctttacaaac tacattgtct gaaacaagta    840
tgcggtacta catacacatt gtaccccctc tgtcctaaaa aaaaaaaaa                889
```

<210> SEQ ID NO 28
<211> LENGTH: 216
<212> TYPE: PRT
<213> ORGANISM: Triticum aestivum

<400> SEQUENCE: 28

```
Met Gly Ala His Pro Tyr Val Pro Ala Ser Leu Asp Leu Pro Gly Tyr
 1                5                  10                  15

Val Pro Leu Arg Leu Thr Gln Leu Glu Ile Leu Gly Ala Tyr Leu Gly
                20                  25                  30

Thr Ser Leu Phe Val Leu Val Ala Val Trp Leu Leu Ser Gly Arg Cys
            35                  40                  45

Arg Arg Leu Ser Gly Thr Asp Arg Leu Leu Met Cys Trp Trp Ala Phe
        50                  55                  60

Thr Gly Leu Thr His Ile Leu Ile Glu Gly Pro Phe Val Phe Thr Pro
65                  70                  75                  80

Asp Phe Phe Thr Lys Thr Asn Pro Asn Phe Phe Asp Glu Val Trp Lys
```

```
                   85                  90                  95
Glu Tyr Ser Lys Gly Asp Ser Arg Tyr Val Ala Arg Asp Thr Ala Thr
                100                 105                 110

Val Thr Val Glu Gly Ile Thr Ala Val Leu Lys Gly Pro Ala Ser Leu
            115                 120                 125

Leu Ala Val Tyr Ala Ile Ala Ser Arg Lys Ser Tyr Ser His Ile Leu
130                 135                 140

Gln Phe Ala Val Cys Leu Gly Gln Leu Tyr Gly Cys Ile Val Tyr Phe
145                 150                 155                 160

Thr Thr Ala Tyr Leu Asp Gly Phe Asn Phe Trp Ala Ser Pro Phe Tyr
                165                 170                 175

Phe Trp Ala Tyr Phe Ile Gly Ala Asn Ser Ser Trp Ile Val Ile Pro
            180                 185                 190

Leu Leu Ile Ala Thr Arg Ser Trp Lys Lys Ile Cys Ala Ala Val His
        195                 200                 205

Gln Ser Glu Lys Val Lys Thr Lys
    210                 215
```

<210> SEQ ID NO 29
<211> LENGTH: 804
<212> TYPE: DNA
<213> ORGANISM: Zea mays

<400> SEQUENCE: 29

```
gcacgaggag cacgacagca taagatccaa caaaggcaag gaggagtgct tgacttcaga      60
agactacaag aagatggaat atcccaaca  agtcatcaac gaggcgctga gatgcggcaa     120
catcgtcaag ttcgtccacc ggaaggcgct gaaagacgtc aaatacaaag agtatctgat    180
tccatctggc tggaaggtcc taccggtctt cactgccgtt catctgaacc cctcacttca    240
tggagacgcg cagcagtttc agccctgtag gtgggagggc acaagccaag gacaagcaa    300
gaggtttaca ccgttcggtg gtggcccccg gctctgccca ggatcagagc tcgctaaagt   360
ggagactgct ttcttcctcc atcaccttgt cctcaattat agatgaggaa ttgatggcga   420
tgacattcca atggcatacc cgtatgtgga gtttcagaga ggtctgccaa tagaaatcga   480
gccaacgtcc cctgaatctt gactgtcctg gagctcagc  catcagttat cacaccagag   540
agaaaagggg aaggtgcatg gagtatacat gaatggtcag tgacagatct cacaagtgaa   600
ggaacactga gggcgcgtgc tagtagctag catatgaggc agctgagact gtaatttaat   660
gtacatggtg tagatatatt ttgtccatgg caattgcttg aagtggctga ttcacttcac   720
cctgtaaaac attctccagt ggtttcaact gctatcctat aaaaagaag  ggccctgtg    780
tttagtaaaa aaaaaaaaa  aaaa                                           804
```

<210> SEQ ID NO 30
<211> LENGTH: 164
<212> TYPE: PRT
<213> ORGANISM: Zea mays

<400> SEQUENCE: 30

```
Glu His Asp Ser Ile Arg Ser Asn Lys Gly Lys Glu Glu Cys Leu Thr
1               5                   10                  15

Ser Glu Asp Tyr Lys Lys Met Glu Tyr Thr Gln Gln Val Ile Asn Glu
            20                  25                  30

Ala Leu Arg Cys Gly Asn Ile Val Lys Phe Val His Arg Lys Ala Leu
        35                  40                  45
```

```
Lys Asp Val Lys Tyr Lys Glu Tyr Leu Ile Pro Ser Gly Trp Lys Val
 50                  55                  60

Leu Pro Val Phe Thr Ala Val His Leu Asn Pro Ser Leu His Gly Asp
 65                  70                  75                  80

Ala Gln Gln Phe Gln Pro Cys Arg Trp Glu Gly Thr Ser Gln Gly Thr
                 85                  90                  95

Ser Lys Arg Phe Thr Pro Phe Gly Gly Gly Pro Arg Leu Cys Pro Gly
            100                 105                 110

Ser Glu Leu Ala Lys Val Glu Thr Ala Phe Phe Leu His His Leu Val
            115                 120                 125

Leu Asn Tyr Arg Trp Arg Ile Asp Gly Asp Asp Ile Pro Met Ala Tyr
            130                 135                 140

Pro Tyr Val Glu Phe Gln Arg Gly Leu Pro Ile Glu Ile Glu Pro Thr
145                 150                 155                 160

Ser Pro Glu Ser

<210> SEQ ID NO 31
<211> LENGTH: 673
<212> TYPE: DNA
<213> ORGANISM: Zea mays
<220> FEATURE:
<221> NAME/KEY: unsure
<222> LOCATION: (3)
<220> FEATURE:
<221> NAME/KEY: unsure
<222> LOCATION: (41)
<220> FEATURE:
<221> NAME/KEY: unsure
<222> LOCATION: (95)
<220> FEATURE:
<221> NAME/KEY: unsure
<222> LOCATION: (227)
<220> FEATURE:
<221> NAME/KEY: unsure
<222> LOCATION: (385)
<220> FEATURE:
<221> NAME/KEY: unsure
<222> LOCATION: (388)
<220> FEATURE:
<221> NAME/KEY: unsure
<222> LOCATION: (390)
<220> FEATURE:
<221> NAME/KEY: unsure
<222> LOCATION: (487)
<220> FEATURE:
<221> NAME/KEY: unsure
<222> LOCATION: (491)
<220> FEATURE:
<221> NAME/KEY: unsure
<222> LOCATION: (554)
<220> FEATURE:
<221> NAME/KEY: unsure
<222> LOCATION: (557)
<220> FEATURE:
<221> NAME/KEY: unsure
<222> LOCATION: (560)
<220> FEATURE:
<221> NAME/KEY: unsure
<222> LOCATION: (626)
<220> FEATURE:
<221> NAME/KEY: unsure
<222> LOCATION: (634)
<220> FEATURE:
<221> NAME/KEY: unsure
<222> LOCATION: (650)
<220> FEATURE:
<221> NAME/KEY: unsure
<222> LOCATION: (664)
<220> FEATURE:
<221> NAME/KEY: unsure
<222> LOCATION: (668)
```

<400> SEQUENCE: 31

```
ggncacgagg ggaagactac aaggaaatgg ttttcacgca ngtggttata aacgagacat      60
tgcggctcgg caacgtggtc aggttcctgc accgngaagt catccgagat gtacactaca    120
atgggtacga cataccgcgg gggtggaaaa tcctgccggt tctagcggcg gtgcacctgg    180
actcgtcgct gtacgaggac cccagccggt tcaacccttg ggagatngga agctggcaga    240
gcaacaacgc gccaagcagc ttcatgccgt acggcggcgg ccgcggctg tgcgccgggt     300
cggagctggc caagctggag atggccatct tcctgcacca cctggtgctc aacttccggt    360
gggagctggc ggacgaccag gcctncgncn acccttcgt cgacttcccc aagggcctcc     420
cgatcagggt ccagcgggtc gccgacgacc aaggccatcg tagcgttttg accgagagca    480
caagagntga nagggaggag cagttcaatt tttcgttgca ttttagggct gtgtctcgtg    540
ttatgagatt gtantantan attatacata ctaaacaaga tagaagcact atgacagagc    600
aaagagagat gtcaaaatgt ttgggngata aatngactca taggtttaan agccgtcatg    660
ccantaaant cta                                                       673
```

<210> SEQ ID NO 32
<211> LENGTH: 145
<212> TYPE: PRT
<213> ORGANISM: Zea mays
<220> FEATURE:
<221> NAME/KEY: UNSURE
<222> LOCATION: (1)
<220> FEATURE:
<221> NAME/KEY: UNSURE
<222> LOCATION: (13)
<220> FEATURE:
<221> NAME/KEY: UNSURE
<222> LOCATION: (75)
<220> FEATURE:
<221> NAME/KEY: UNSURE
<222> LOCATION: (128)..(130)

<400> SEQUENCE: 32

```
Xaa Arg Gly Glu Asp Tyr Lys Glu Met Val Phe Thr Xaa Val Val Ile
  1               5                  10                  15
Asn Glu Thr Leu Arg Leu Gly Asn Val Val Arg Phe Leu His Arg Glu
             20                  25                  30
Val Ile Arg Asp Val His Tyr Asn Gly Tyr Asp Ile Pro Arg Gly Trp
         35                  40                  45
Lys Ile Leu Pro Val Leu Ala Ala Val His Leu Asp Ser Ser Leu Tyr
     50                  55                  60
Glu Asp Pro Ser Arg Phe Asn Pro Trp Glu Xaa Gly Ser Trp Gln Ser
 65                  70                  75                  80
Asn Asn Ala Pro Ser Ser Phe Met Pro Tyr Gly Gly Pro Arg Leu
                 85                  90                  95
Cys Ala Gly Ser Glu Leu Ala Lys Leu Glu Met Ala Ile Phe Leu His
                100                 105                 110
His Leu Val Leu Asn Phe Arg Trp Glu Leu Ala Asp Asp Gln Ala Xaa
            115                 120                 125
Xaa Xaa Pro Phe Val Asp Phe Pro Lys Gly Leu Pro Ile Arg Val Gln
        130                 135                 140
Arg
145
```

<210> SEQ ID NO 33

```
<211> LENGTH: 616
<212> TYPE: DNA
<213> ORGANISM: Zea mays
<220> FEATURE:
<221> NAME/KEY: unsure
<222> LOCATION: (387)
<220> FEATURE:
<221> NAME/KEY: unsure
<222> LOCATION: (415)
<220> FEATURE:
<221> NAME/KEY: unsure
<222> LOCATION: (489)
<220> FEATURE:
<221> NAME/KEY: unsure
<222> LOCATION: (491)
<220> FEATURE:
<221> NAME/KEY: unsure
<222> LOCATION: (544)
<220> FEATURE:
<221> NAME/KEY: unsure
<222> LOCATION: (551)
<220> FEATURE:
<221> NAME/KEY: unsure
<222> LOCATION: (558)
<220> FEATURE:
<221> NAME/KEY: unsure
<222> LOCATION: (562)
<220> FEATURE:
<221> NAME/KEY: unsure
<222> LOCATION: (567)
<220> FEATURE:
<221> NAME/KEY: unsure
<222> LOCATION: (569)
<220> FEATURE:
<221> NAME/KEY: unsure
<222> LOCATION: (592)
<220> FEATURE:
<221> NAME/KEY: unsure
<222> LOCATION: (600)
<220> FEATURE:
<221> NAME/KEY: unsure
<222> LOCATION: (611)
<220> FEATURE:
<221> NAME/KEY: unsure
<222> LOCATION: (616)

<400> SEQUENCE: 33
gagacaaagg ctaaggggggg cgtccaaatt gagctgggaa gactacaagg aaatggtttt      60
cacgcagtgt gttataaacg agacattgcg gctcggcaac gtggtcaggt tcctgcaccg     120
gaaggtcatc cgagatgtac actacaatgg gtacgacata ccgcgggggt ggaaaatcct     180
gccggttcta gcggcggtgc acctggactc gtcgctgtac gaggacccca gccggttcaa     240
cccttggaga tggaagagca caacgcgcc aagcagcttc atgccgtacg gcggcgggcc     300
gcggctgtgc gccgggtcgg agctggcaag ctggagatgg catcttcctg cacacctggt     360
gctcaacttc cggtgggact ggcggancgg acaagccttc gtcaaccttt cgtcnattcc     420
caaggctcca taggtcaacg gtcccgacac aagcacgtac gtttgccgag acacagagtg     480
aaggagagna ntaatttctt catttgaggg tgtggcctgt ttagtaatgg atatatattc     540
tcanacagat nacacttnaa gncaagngng tgcaaatttg ggaaaatttc cncaggttan     600
agcgcagcca ntatan                                                     616

<210> SEQ ID NO 34
<211> LENGTH: 126
<212> TYPE: PRT
<213> ORGANISM: Zea mays

<400> SEQUENCE: 34

Arg Gln Arg Leu Arg Gly Ala Ser Lys Leu Ser Trp Glu Asp Tyr Lys
```

|   | 1 |   |   | 5 |   |   |   | 10 |   |   |   | 15 |   |
|---|---|---|---|---|---|---|---|---|---|---|---|---|---|
| Glu | Met | Val | Phe | Thr | Gln | Cys | Val | Ile | Asn | Glu | Thr | Leu | Arg | Leu | Gly |

Asn Val Val Arg Phe Leu His Arg Lys Val Ile Arg Asp Val His Tyr
     35                  40                  45

Asn Gly Tyr Asp Ile Pro Arg Gly Trp Lys Ile Leu Pro Val Leu Ala
 50                  55                  60

Ala Val His Leu Asp Ser Ser Leu Tyr Glu Asp Pro Ser Arg Phe Asn
 65                  70                  75                  80

Pro Trp Arg Trp Lys Ser Asn Asn Ala Pro Ser Ser Phe Met Pro Tyr
             85                  90                  95

Gly Gly Gly Pro Arg Leu Cys Ala Gly Ser Glu Leu Ala Ser Trp Arg
             100                 105                 110

Trp His Leu Pro Ala His Leu Val Leu Asn Phe Arg Trp Asp
         115                 120                 125

<210> SEQ ID NO 35
<211> LENGTH: 1181
<212> TYPE: DNA
<213> ORGANISM: Oryza sativa

<400> SEQUENCE: 35

```
gcacgaggca gaacgagggg aggctgttcg agtgcagcta cccgcgcagc atcggcggca      60
tcctgggcaa gtggtccatg ctggtcctcg tcggggaccc gcaccgcgag atgcgcgcca     120
tctccctcaa cttcctctcc tccgtccgcc tccgcgccgt cctcctcccc gaggtcgagc     180
gccacaccct cctcgtcctc cgcgcctggc ccccttcctc caccttctcc gctcagcacc     240
aagccaagaa gttcacgttc aacctgatgg cgaagaacat aatgagcatg gacccggggg     300
aggaagagac ggagcggctg cggcgggagt acatcacctt catgaagggc gtggtctccg     360
cgccgctcaa cctgcccggg acgccctact ggaaggctct caagtcgcgt gctgccattc     420
tcggagtaat agagaggaaa atggaagagc gggttgagaa gctgagcaag gaggatgcaa     480
gcgtagagca agacgatctt ctcggatggg ctctgaaaca atctaaccct tcaaaagagc     540
aaatcctgga cctcttgctg agcttgctct tcgccgggca cgagacgtcg tccatggcgc     600
tcgccctcgc catcttcttc cttgaaggct gccccaaggc tgtccaagaa ctgaggaagg     660
agcatcttgg gattgcaagg agacaaaggc taagagggga gtgcaaattg agctgggaag     720
actacaaaga gatggttttc acgcaatgtg tcataaacga gacgttgcgg ctaggaaacg     780
tggtcaggtt cctgcaccgg aaggtcatca aggacgtgca ctacaagggt tatgacattc     840
caagcggatg gaagatcctg ccggtgttag ccgcggtgca tctggactcg tccctgtacg     900
aggacccca gcgcttcaat ccctggagat ggaagagtag cggatcatcc ggcggcttgg     960
ctcagagcag cagcttcatg ccgtacggcg gcgggacgcg gctgtgcgcc gggtcggagc    1020
tcgcgaagct ggagatggcc gtgttcttgc accacctggt gctcaacttc aggtgggagc    1080
tcgccgagcc ggaccaagcc ttcgtcttcc ccttcgtcga cttccccaag ggccttccca    1140
ttagggttca tagaattgca caggatgatg agcaggagta a                       1181
```

<210> SEQ ID NO 36
<211> LENGTH: 392
<212> TYPE: PRT
<213> ORGANISM: Oryza sativa

<400> SEQUENCE: 36

-continued

```
Thr Arg Gln Asn Glu Gly Arg Leu Phe Glu Cys Ser Tyr Pro Arg Ser
 1               5                  10                  15

Ile Gly Gly Ile Leu Gly Lys Trp Ser Met Leu Val Leu Val Gly Asp
                20                  25                  30

Pro His Arg Glu Met Arg Ala Ile Ser Leu Asn Phe Leu Ser Ser Val
                35                  40                  45

Arg Leu Arg Ala Val Leu Leu Pro Glu Val Arg His Thr Leu Leu
 50                  55                  60

Val Leu Arg Ala Trp Pro Pro Ser Ser Thr Phe Ser Ala Gln His Gln
 65                  70                  75                  80

Ala Lys Lys Phe Thr Phe Asn Leu Met Ala Lys Asn Ile Met Ser Met
                85                  90                  95

Asp Pro Gly Glu Glu Thr Glu Arg Leu Arg Arg Glu Tyr Ile Thr
                100                 105                 110

Phe Met Lys Gly Val Val Ser Ala Pro Leu Asn Leu Pro Gly Thr Pro
                115                 120                 125

Tyr Trp Lys Ala Leu Lys Ser Arg Ala Ala Ile Leu Gly Val Ile Glu
                130                 135                 140

Arg Lys Met Glu Glu Arg Val Glu Lys Leu Ser Lys Glu Asp Ala Ser
145                 150                 155                 160

Val Glu Gln Asp Asp Leu Leu Gly Trp Ala Leu Lys Gln Ser Asn Leu
                165                 170                 175

Ser Lys Glu Gln Ile Leu Asp Leu Leu Ser Leu Leu Phe Ala Gly
                180                 185                 190

His Glu Thr Ser Ser Met Ala Leu Ala Leu Ala Ile Phe Phe Leu Glu
                195                 200                 205

Gly Cys Pro Lys Ala Val Gln Glu Leu Arg Lys Glu His Leu Gly Ile
    210                 215                 220

Ala Arg Arg Gln Arg Leu Arg Gly Glu Cys Lys Leu Ser Trp Glu Asp
225                 230                 235                 240

Tyr Lys Glu Met Val Phe Thr Gln Cys Val Ile Asn Glu Thr Leu Arg
                245                 250                 255

Leu Gly Asn Val Val Arg Phe Leu His Arg Lys Val Ile Lys Asp Val
                260                 265                 270

His Tyr Lys Gly Tyr Asp Ile Pro Ser Gly Trp Lys Ile Leu Pro Val
                275                 280                 285

Leu Ala Ala Val His Leu Asp Ser Ser Leu Tyr Glu Asp Pro Gln Arg
    290                 295                 300

Phe Asn Pro Trp Arg Trp Lys Ser Ser Gly Ser Gly Leu Ala
305                 310                 315                 320

Gln Ser Ser Ser Phe Met Pro Tyr Gly Gly Gly Thr Arg Leu Cys Ala
                325                 330                 335

Gly Ser Glu Leu Ala Lys Leu Glu Met Ala Val Phe Leu His His Leu
                340                 345                 350

Val Leu Asn Phe Arg Trp Glu Leu Ala Glu Pro Asp Gln Ala Phe Val
                355                 360                 365

Phe Pro Phe Val Asp Phe Pro Lys Gly Leu Pro Ile Arg Val His Arg
    370                 375                 380

Ile Ala Gln Asp Asp Glu Gln Glu
385                 390

<210> SEQ ID NO 37
<211> LENGTH: 577
<212> TYPE: DNA
```

```
<213> ORGANISM: Glycine max
<220> FEATURE:
<221> NAME/KEY: unsure
<222> LOCATION: (228)
<220> FEATURE:
<221> NAME/KEY: unsure
<222> LOCATION: (323)
<220> FEATURE:
<221> NAME/KEY: unsure
<222> LOCATION: (429)
<220> FEATURE:
<221> NAME/KEY: unsure
<222> LOCATION: (460)
<220> FEATURE:
<221> NAME/KEY: unsure
<222> LOCATION: (488)
<220> FEATURE:
<221> NAME/KEY: unsure
<222> LOCATION: (499)
<220> FEATURE:
<221> NAME/KEY: unsure
<222> LOCATION: (510)
<220> FEATURE:
<221> NAME/KEY: unsure
<222> LOCATION: (517)
<220> FEATURE:
<221> NAME/KEY: unsure
<222> LOCATION: (520)
<220> FEATURE:
<221> NAME/KEY: unsure
<222> LOCATION: (524)
<220> FEATURE:
<221> NAME/KEY: unsure
<222> LOCATION: (534)
<220> FEATURE:
<221> NAME/KEY: unsure
<222> LOCATION: (536)
<220> FEATURE:
<221> NAME/KEY: unsure
<222> LOCATION: (542)
<220> FEATURE:
<221> NAME/KEY: unsure
<222> LOCATION: (546)
<220> FEATURE:
<221> NAME/KEY: unsure
<222> LOCATION: (552)
<220> FEATURE:
<221> NAME/KEY: unsure
<222> LOCATION: (559)
<220> FEATURE:
<221> NAME/KEY: unsure
<222> LOCATION: (561)

<400> SEQUENCE: 37
gaggtaccaa ccactctttt ttacttatgg catctttcat cttcacacct gtactctttc      60
ttcttatcat ctccgccgtc cttctcttcc tccaccgccg atcccgctgc cggcgcttcc     120
gcctaccgcc tggtacactc gggctcccct tcgtcggcga aaccttacag ctcatatcag     180
cttacaagag tgacaacccg gaaccttca tggaccagcg cgtgaaaggg tacggtccaa      240
tcttcaccac ccatgtgttc ggcgaaccca ccgtgttctc gaccgaccca gaaacgaacc     300
ggttcatttt gctcaacgaa ggnaagctct tcgaatgcag ctacccggt tcgatatcga      360 acctccttgg gaaacactct ctgctcctca tgaaaggttt cttcacaaga gaatgatcct     420
actatgagnt gcaactctcc atcataagga cattattggn gcatgacgct atcggatact     480
tggattcngg tcgccgggnc tttatgagan caagaantan gttngtgcag taanantgtg     540
anttgncagg gnatggctng nctaggagag acggctg                             577

<210> SEQ ID NO 38
<211> LENGTH: 124
<212> TYPE: PRT
```

```
<213> ORGANISM: Glycine max
<220> FEATURE:
<221> NAME/KEY: UNSURE
<222> LOCATION: (68)

<400> SEQUENCE: 38

Met Ala Ser Phe Ile Phe Thr Pro Val Leu Phe Leu Ile Ile Ser
 1               5                  10                  15

Ala Val Leu Leu Phe Leu His Arg Arg Ser Arg Cys Arg Arg Phe Arg
                20                  25                  30

Leu Pro Pro Gly Thr Leu Gly Leu Pro Phe Val Gly Glu Thr Leu Gln
            35                  40                  45

Leu Ile Ser Ala Tyr Lys Ser Asp Asn Pro Glu Pro Phe Met Asp Gln
        50                  55                  60

Arg Val Lys Xaa Tyr Gly Pro Ile Phe Thr Thr His Val Phe Gly Glu
 65                 70                  75                  80

Pro Thr Val Phe Ser Thr Asp Pro Glu Thr Asn Arg Phe Ile Leu Leu
                85                  90                  95

Asn Glu Gly Lys Leu Phe Glu Cys Ser Tyr Pro Gly Ser Ile Ser Asn
            100                 105                 110

Leu Leu Gly Lys His Ser Leu Leu Leu Met Lys Gly
        115                 120

<210> SEQ ID NO 39
<211> LENGTH: 600
<212> TYPE: DNA
<213> ORGANISM: Triticum aestivum

<400> SEQUENCE: 39
gcacgagctt caaccctngg agatggaagg gcaacgcatc cggcgtggcg cagaacagca      60
acttcatgcc ctacggcggc ggcaccaggc tctgcgccgg gtcggagctc gccaagctcg     120
agatggccat cttcctgcac cacctggtgc tcaacttccg gtgggagctc gccgagccgg     180
accaggcgtt cgtctacccg ttcgtcgact tccccaaggg cctgcccatc agggtccata     240
ggattgcaca ggaggaagaa ggagaagagt aaagcgtttt gaccgtggac atatatgatc     300
ggtgcttcag tctagcgtct aggggagagt atacagagga aatgtacaca tgtccgtcct     360
tgttttcttt ccctttgggg tttgtgttat gtagatggga taaacaaaga tgctagggta     420
ttaccataag aggaaatgtt ggtaggatca gcaagtagag ttgtaataag gccggcccac     480
agcccactag taagtgattc caaagagtag gcctagcggt cttgctatct tcttgcctcg     540
ttcctccagc caatccatat ttgattctta aaaaaaggc aattcatatt ttgcctaaaa      600

<210> SEQ ID NO 40
<211> LENGTH: 89
<212> TYPE: PRT
<213> ORGANISM: Triticum aestivum

<400> SEQUENCE: 40

Thr Ser Phe Asn Pro Trp Arg Trp Lys Gly Asn Ala Ser Gly Val Ala
 1               5                  10                  15

Gln Asn Ser Asn Phe Met Pro Tyr Gly Gly Gly Thr Arg Leu Cys Ala
                20                  25                  30

Gly Ser Glu Leu Ala Lys Leu Glu Met Ala Ile Phe Leu His His Leu
            35                  40                  45

Val Leu Asn Phe Arg Trp Glu Leu Ala Glu Pro Asp Gln Ala Phe Val
        50                  55                  60
```

```
Tyr Pro Phe Val Asp Phe Pro Lys Gly Leu Pro Ile Arg Val His Arg
 65                  70                  75                  80

Ile Ala Gln Glu Glu Glu Gly Glu Glu
                 85
```

<210> SEQ ID NO 41
<211> LENGTH: 1426
<212> TYPE: DNA
<213> ORGANISM: Zea mays

<400> SEQUENCE: 41

```
gcacgagcaa agatctgaat aataatgggt tcgctccgtg atggcaagac caacagcagc     60
agtggccggc ggtggtgcgc ggtgaccggc ggccggggct tcatggcgag caccggtg     120
gccgcgctgc tgcgctccgg cgagtggctt gtgcgggtca ccgacctcgc cccggatgtc    180
gtgctcggcc tcggcgacac cgaggacgtc tcgatgacg ccctccgtga tggccgcgcc    240
gtctatgcct cagcggatgt ctgcaaccta gaccagctta ttcaagcttt tgaaggggtt    300
gaggttgttt tccacacagc tgctgcggat ccaagcaaga acgaccagca acttcactat    360
aaggtcaacg ttgagggac aaagaacgtg gttgatgcgt gcatgatttg caaggtgaaa    420
aggcttatcc acaccagctc tattgctgtt gtgttcgacg gagttaatgg gcttctcgat    480
gcaaatgaat cattgccata cccagacaag tttcctgatg cgtatggaca aacaaaggca    540
gaagcagaaa agatagtcat gaaggctaat ggcattagtg gccttctaac ttgttgcata    600
cgtcctggta gcattttgg ccctggtgac atagttatac taccaactct ggaccaatgt    660
ggaaaaacac actttgtttt tggtgatggg aagaattgtg atgattttgt atatgttgaa    720
aatgtggtac atggccacat ttgtgctgaa aaaactcttt ctacaatgga aggcgcaaaa    780
accagtggtg gaaaagccta ctttataacc aatacggaac caatgaacat gtgggacttt    840
ctatatctgc ttcaagaaga acttggatac aaaaggttgt tcaagataag aatacctttg    900
attgtcatcc aggcagtaag ctatttggta gagtggggat acaaggttct acaccattat    960
ggaatgtgcc agcctcaagt gctaacacca gcaaggatca agtatctgac agttcataga   1020
acattcagtt gtaacaaagc tgctgaagaa cttggctaca aaccaattgt gacacttatg   1080
gatggtatga agctagcagt caaatcatat attcggttga gaaatcatgc agatttatct   1140
tacaaacata tataaaagat tatcattatg gcataggatg cctcatgctg acgatataca   1200
acagcttttg agaattgtca taagcgaagg tctgccgtga ttatgtttcc aataaataaa   1260
aaattcggtg tttacaactc gcatcaatgt cctgatcaaa acccagcat gttgtattct   1320
gatttagtag caaagataga ttgtaactcc ttaacaatga tcaggcatgt atttcagata   1380
tgttaattgg aacacaaata atattactaa aaaaaaaaaa aaaaaa                  1426
```

<210> SEQ ID NO 42
<211> LENGTH: 376
<212> TYPE: PRT
<213> ORGANISM: Zea mays

<400> SEQUENCE: 42

```
Met Gly Ser Leu Arg Asp Gly Lys Thr Asn Ser Ser Gly Arg Arg
 1               5                  10                  15

Trp Cys Ala Val Thr Gly Gly Arg Gly Phe Met Ala Arg His Leu Val
                20                  25                  30

Ala Ala Leu Leu Arg Ser Gly Glu Trp Leu Val Arg Val Thr Asp Leu
            35                  40                  45
```

Ala Pro Asp Val Val Leu Gly Leu Gly Asp Thr Glu Asp Val Leu Asp
                50                  55                  60

Asp Ala Leu Arg Asp Gly Arg Ala Val Tyr Ala Ser Ala Asp Val Cys
 65                  70                  75                  80

Asn Leu Asp Gln Leu Ile Gln Ala Phe Glu Gly Val Glu Val Phe
                85                  90                  95

His Thr Ala Ala Ala Asp Pro Ser Lys Asn Asp Gln Gln Leu His Tyr
            100                 105                 110

Lys Val Asn Val Glu Gly Thr Lys Asn Val Val Asp Ala Cys Met Ile
            115                 120                 125

Cys Lys Val Lys Arg Leu Ile His Thr Ser Ser Ile Ala Val Val Phe
130                 135                 140

Asp Gly Val Asn Gly Leu Leu Asp Ala Asn Glu Ser Leu Pro Tyr Pro
145                 150                 155                 160

Asp Lys Phe Pro Asp Ala Tyr Gly Gln Thr Lys Ala Glu Ala Glu Lys
                165                 170                 175

Ile Val Met Lys Ala Asn Gly Ile Ser Gly Leu Leu Thr Cys Cys Ile
            180                 185                 190

Arg Pro Gly Ser Ile Phe Gly Pro Gly Asp Ile Val Ile Leu Pro Thr
            195                 200                 205

Leu Asp Gln Cys Gly Lys Thr His Phe Val Phe Gly Asp Gly Lys Asn
210                 215                 220

Cys Asp Asp Phe Val Tyr Val Glu Asn Val Val His Gly His Ile Cys
225                 230                 235                 240

Ala Glu Lys Thr Leu Ser Thr Met Glu Gly Ala Lys Thr Ser Gly Gly
                245                 250                 255

Lys Ala Tyr Phe Ile Thr Asn Thr Glu Pro Met Asn Met Trp Asp Phe
            260                 265                 270

Leu Tyr Leu Leu Gln Glu Glu Leu Gly Tyr Lys Arg Leu Phe Lys Ile
            275                 280                 285

Arg Ile Pro Leu Ile Val Ile Gln Ala Val Ser Tyr Leu Val Glu Trp
290                 295                 300

Gly Tyr Lys Val Leu His His Tyr Gly Met Cys Gln Pro Gln Val Leu
305                 310                 315                 320

Thr Pro Ala Arg Ile Lys Tyr Leu Thr Val His Arg Thr Phe Ser Cys
                325                 330                 335

Asn Lys Ala Ala Glu Glu Leu Gly Tyr Lys Pro Ile Val Thr Leu Met
            340                 345                 350

Asp Gly Met Lys Leu Ala Val Lys Ser Tyr Ile Arg Leu Arg Asn His
            355                 360                 365

Ala Asp Leu Ser Tyr Lys His Ile
            370                 375

<210> SEQ ID NO 43
<211> LENGTH: 1663
<212> TYPE: DNA
<213> ORGANISM: Glycine max
<220> FEATURE:
<221> NAME/KEY: unsure
<222> LOCATION: (1407)
<220> FEATURE:
<221> NAME/KEY: unsure
<222> LOCATION: (1429)

<400> SEQUENCE: 43
gcacgaggtt ggaatgaggt gagcgttgtg tttgagttag cttgactatg gaagcaaaag        60

-continued

| | |
|---|---|
| ataagtggtg cgtggtgacc ggaggtcgcg gcttcgctgc tcggcatttg gtggaaatgc | 120 |
| taattcgtca caaggagtac tgcgttcgca tcgccgattt ggaagtcagc attgttctcg | 180 |
| agcccgccga gcagttaggc cttctcggcc aggccctgca ctctggccga gcccaatatg | 240 |
| tctccctcga tcttcgcaac aaggcccaag ttctaaaagc gttggaggga gttgaggtgg | 300 |
| tgttccacat ggctgctcca aactcttcca ttaacaacta ccagcttcat cattccgtca | 360 |
| atgtgcaagg gacgaataat gtcatcgatg cttgcgtgga gctgaacgtg aagcgtctcg | 420 |
| tttacactag ctgtctcgtt tacaccagct ctcccagcgt cttcttcgac gatgttcatg | 480 |
| gaattcataa tggaaacgaa acaatgcctt atgcgcattc gcctaatgat cattattcag | 540 |
| caacgaaagc cgaggctgag gcattggtta ttaaagctaa tgggactaat gggctcctaa | 600 |
| cgtgctgcat acgccctagc agcattttg gcctggtga taggctgtcg gtgccttcac | 660 |
| tagttgatgc tgccagaaaa ggggaatcta agtttcttat tggtgatggc aataacgttt | 720 |
| atgatttcac atatgttgaa atgtggctc atgcccatat atgtgctgat cgagctctag | 780 |
| cttcagaagg accggtttca gaaaaagctg cgggagaggc atatttcata acaaatatgg | 840 |
| agcctatgaa attctgggag ttcgtgtcat tggtagtgga aggtcttgga tatgaaaggc | 900 |
| caaggataaa gatccccacc tttgttatca tgcccattgc acatttggtg gagtggatat | 960 |
| ataagctgct aggcccatat gggatgaagc tgcctcagtt aattccttcg agaataagac | 1020 |
| tcatatcttg cagcagaact tttgattgct caaaagcaaa ggatcgcctt ggctatgcac | 1080 |
| ccatcgtaac actacaggag ggtctgcgaa ggacaattga atcatacaca cacttgaggg | 1140 |
| cggataatga acctaaaact aaaagagaag gtccctcaaa agcttccaaa tatcttggaa | 1200 |
| gtggaagagg tgtgaataat caactatatc tgtctaactt ctttgcttgg tgatgaggat | 1260 |
| caaacaagga ataaataaat tgaagaagac taatttttta ttaaataaag tttgtaatat | 1320 |
| ttagtgagac ataataaaag tgactgttgc ctcactaaaa aaaaaaaaa aaaaaaaaa | 1380 |
| aaaacacaac aaaaaaaaaa aaaaaanaac aaaaaaaaaa acaacaacna aaaaaaaaac | 1440 |
| cccccgggg gggggggccg ggaccccaaa ttccccccaa aaagtgggct ctttataacc | 1500 |
| cccgccccaa tgggcctgtc ttttttaaaa actctcggtg agtggggaaa aacccttggg | 1560 |
| ggtaacccaa ctttaaatcc cccttttggaa aaaaatcccc cttttttccc aaaggtgggg | 1620 |
| ttataaaaaa aaaaagagcc cccacacttt tttcccctttt cca | 1663 |

<210> SEQ ID NO 44
<211> LENGTH: 401
<212> TYPE: PRT
<213> ORGANISM: Glycine max

<400> SEQUENCE: 44

```
Met Glu Ala Lys Asp Lys Trp Cys Val Val Thr Gly Gly Arg Gly Phe
  1               5                  10                  15

Ala Ala Arg His Leu Val Glu Met Leu Ile Arg His Lys Glu Tyr Cys
             20                  25                  30

Val Arg Ile Ala Asp Leu Glu Val Ser Ile Val Leu Glu Pro Ala Glu
         35                  40                  45

Gln Leu Gly Leu Leu Gly Gln Ala Leu His Ser Gly Arg Ala Gln Tyr
     50                  55                  60

Val Ser Leu Asp Leu Arg Asn Lys Ala Gln Val Leu Lys Ala Leu Glu
 65                  70                  75                  80

Gly Val Glu Val Val Phe His Met Ala Ala Pro Asn Ser Ser Ile Asn
                 85                  90                  95
```

```
Asn Tyr Gln Leu His His Ser Val Asn Val Gln Gly Thr Asn Asn Val
            100                 105                 110

Ile Asp Ala Cys Val Glu Leu Asn Val Lys Arg Leu Val Tyr Thr Ser
        115                 120                 125

Cys Leu Val Tyr Thr Ser Ser Pro Ser Val Phe Phe Asp Asp Val His
    130                 135                 140

Gly Ile His Asn Gly Asn Glu Thr Met Pro Tyr Ala His Ser Pro Asn
145                 150                 155                 160

Asp His Tyr Ser Ala Thr Lys Ala Glu Ala Glu Ala Leu Val Ile Lys
                165                 170                 175

Ala Asn Gly Thr Asn Gly Leu Leu Thr Cys Cys Ile Arg Pro Ser Ser
            180                 185                 190

Ile Phe Gly Pro Gly Asp Arg Leu Ser Val Pro Ser Leu Val Asp Ala
        195                 200                 205

Ala Arg Lys Gly Glu Ser Lys Phe Leu Ile Gly Asp Gly Asn Asn Val
    210                 215                 220

Tyr Asp Phe Thr Tyr Val Glu Asn Val Ala His Ala His Ile Cys Ala
225                 230                 235                 240

Asp Arg Ala Leu Ala Ser Glu Gly Pro Val Ser Glu Lys Ala Ala Gly
            245                 250                 255

Glu Ala Tyr Phe Ile Thr Asn Met Glu Pro Met Lys Phe Trp Glu Phe
            260                 265                 270

Val Ser Leu Val Val Glu Gly Leu Gly Tyr Glu Arg Pro Arg Ile Lys
        275                 280                 285

Ile Pro Thr Phe Val Ile Met Pro Ile Ala His Leu Val Glu Trp Ile
    290                 295                 300

Tyr Lys Leu Leu Gly Pro Tyr Gly Met Lys Leu Pro Gln Leu Ile Pro
305                 310                 315                 320

Ser Arg Ile Arg Leu Ile Ser Cys Ser Arg Thr Phe Asp Cys Ser Lys
            325                 330                 335

Ala Lys Asp Arg Leu Gly Tyr Ala Pro Ile Val Thr Leu Gln Glu Gly
            340                 345                 350

Leu Arg Arg Thr Ile Glu Ser Tyr Thr His Leu Arg Ala Asp Asn Glu
        355                 360                 365

Pro Lys Thr Lys Arg Glu Gly Pro Ser Lys Ala Ser Lys Tyr Leu Gly
    370                 375                 380

Ser Gly Arg Gly Val Asn Asn Gln Leu Tyr Leu Ser Asn Phe Phe Ala
385                 390                 395                 400

Trp
```